(12) United States Patent
Wu et al.

(10) Patent No.: US 8,952,023 B1
(45) Date of Patent: Feb. 10, 2015

(54) COMPOUNDS USEFUL FOR TREATING INJURIES FROM WARFARE AGENTS

(71) Applicants: Xinyuan Wu, Newton, MA (US); Spencer David Kimball, East Windsor, NJ (US)

(72) Inventors: Xinyuan Wu, Newton, MA (US); Spencer David Kimball, East Windsor, NJ (US)

(73) Assignee: Hydra Biosciences, Inc., Cambridge, MA (US)

( * ) Notice: Subject to any disclaimer, the term of this patent is extended or adjusted under 35 U.S.C. 154(b) by 0 days.

(21) Appl. No.: 13/861,858

(22) Filed: Apr. 12, 2013

Related U.S. Application Data

(63) Continuation of application No. 12/696,723, filed on Jan. 29, 2010, now abandoned.

(60) Provisional application No. 61/148,296, filed on Jan. 29, 2009.

(51) Int. Cl.
  *A61K 31/519* (2006.01)
  *C07D 239/70* (2006.01)
  *C07D 471/04* (2006.01)

(52) U.S. Cl.
  CPC ............ *C07D 471/04* (2013.01); *A61K 31/519* (2013.01); *C07D 239/70* (2013.01)
  USPC ...................................................... 514/267

(58) Field of Classification Search
  CPC ... A61K 31/519; C07D 239/70; C07D 471/04
  USPC ........................................................ 514/267
  See application file for complete search history.

(56) References Cited

U.S. PATENT DOCUMENTS 8,530,487 B1 * 9/2013 Wu et al. .................... 514/267

* cited by examiner

*Primary Examiner* — Erich A Leeser
(74) *Attorney, Agent, or Firm* — Lando & Anastasi LLP

(57) ABSTRACT

Compounds and compositions for treating disorders related to TRPA1 are described herein.

10 Claims, No Drawings

SEQUENCE LISTING

<160> NUMBER OF SEQ ID NOS: 6

<210> SEQ ID NO 1
<211> LENGTH: 1119
<212> TYPE: PRT
<213> ORGANISM: Homo sapiens

<400> SEQUENCE: 1

```
Met Lys Arg Ser Leu Arg Lys Met Trp Arg Pro Gly Glu Lys Lys Glu
 1               5                  10                  15

Pro Gln Gly Val Val Tyr Glu Asp Val Pro Asp Asp Thr Glu Asp Phe
            20                  25                  30

Lys Glu Ser Leu Lys Val Val Phe Glu Gly Ser Ala Tyr Gly Leu Gln
        35                  40                  45

Asn Phe Asn Lys Gln Lys Lys Leu Lys Arg Cys Asp Asp Met Asp Thr
    50                  55                  60

Phe Phe Leu His Tyr Ala Ala Glu Gly Gln Ile Glu Leu Met Glu
65                  70                  75                  80

Lys Ile Thr Arg Asp Ser Ser Leu Glu Val Leu His Glu Met Asp Asp
                85                  90                  95

Tyr Gly Asn Thr Pro Leu His Cys Ala Val Glu Lys Asn Gln Ile Glu
            100                 105                 110

Ser Val Lys Phe Leu Leu Ser Arg Gly Ala Asn Pro Asn Leu Arg Asn
        115                 120                 125

Phe Asn Met Met Ala Pro Leu His Ile Ala Val Gln Gly Met Asn Asn
    130                 135                 140

Glu Val Met Lys Val Leu Leu Glu His Arg Thr Ile Asp Val Asn Leu
145                 150                 155                 160

Glu Gly Glu Asn Gly Asn Thr Ala Val Ile Ile Ala Cys Thr Thr Asn
                165                 170                 175

Asn Ser Glu Ala Leu Gln Ile Leu Leu Asn Lys Gly Ala Lys Pro Cys
            180                 185                 190

Lys Ser Asn Lys Trp Gly Cys Phe Pro Ile His Gln Ala Ala Phe Ser
        195                 200                 205

Gly Ser Lys Glu Cys Met Glu Ile Ile Leu Arg Phe Gly Glu Glu His
    210                 215                 220

Gly Tyr Ser Arg Gln Leu His Ile Asn Phe Met Asn Asn Gly Lys Ala
225                 230                 235                 240

Thr Pro Leu His Leu Ala Val Gln Asn Gly Asp Leu Glu Met Ile Lys
                245                 250                 255

Met Cys Leu Asp Asn Gly Ala Gln Ile Asp Pro Val Glu Lys Gly Arg
            260                 265                 270

Cys Thr Ala Ile His Phe Ala Ala Thr Gln Gly Ala Thr Glu Ile Val
        275                 280                 285

Lys Leu Met Ile Ser Ser Tyr Ser Gly Ser Val Asp Ile Val Asn Thr
    290                 295                 300

Thr Asp Gly Cys His Glu Thr Met Leu His Arg Ala Ser Leu Phe Asp
305                 310                 315                 320

His His Glu Leu Ala Asp Tyr Leu Ile Ser Val Gly Ala Asp Ile Asn
                325                 330                 335

Lys Ile Asp Ser Glu Gly Arg Ser Pro Leu Ile Leu Ala Thr Ala Ser
            340                 345                 350

Ala Ser Trp Asn Ile Val Asn Leu Leu Leu Ser Lys Gly Ala Gln Val
        355                 360                 365
```

-continued

```
Asp Ile Lys Asp Asn Phe Gly Arg Asn Phe Leu His Leu Thr Val Gln
    370                 375                 380

Gln Pro Tyr Gly Leu Lys Asn Leu Arg Pro Glu Phe Met Gln Met Gln
385                 390                 395                 400

Gln Ile Lys Glu Leu Val Met Asp Glu Asp Asn Asp Gly Cys Thr Pro
                405                 410                 415

Leu His Tyr Ala Cys Arg Gln Gly Gly Pro Gly Ser Val Asn Asn Leu
                420                 425                 430

Leu Gly Phe Asn Val Ser Ile His Ser Lys Ser Lys Asp Lys Lys Ser
            435                 440                 445

Pro Leu His Phe Ala Ala Ser Tyr Gly Arg Ile Asn Thr Cys Gln Arg
450                 455                 460

Leu Leu Gln Asp Ile Ser Asp Thr Arg Leu Leu Asn Glu Gly Asp Leu
465                 470                 475                 480

His Gly Met Thr Pro Leu His Leu Ala Ala Lys Asn Gly His Asp Lys
                485                 490                 495

Val Val Gln Leu Leu Leu Lys Lys Gly Ala Leu Phe Leu Ser Asp His
            500                 505                 510

Asn Gly Trp Thr Ala Leu His His Ala Ser Met Gly Gly Tyr Thr Gln
            515                 520                 525

Thr Met Lys Val Ile Leu Asp Thr Asn Leu Lys Cys Thr Asp Arg Leu
            530                 535                 540

Asp Glu Asp Gly Asn Thr Ala Leu His Phe Ala Ala Arg Glu Gly His
545                 550                 555                 560

Ala Lys Ala Val Ala Leu Leu Leu Ser His Asn Ala Asp Ile Val Leu
                565                 570                 575

Asn Lys Gln Gln Ala Ser Phe Leu His Leu Ala Leu His Asn Lys Arg
            580                 585                 590

Lys Glu Val Val Leu Thr Ile Ile Arg Ser Lys Arg Trp Asp Glu Cys
        595                 600                 605

Leu Lys Ile Phe Ser His Asn Ser Pro Gly Asn Lys Cys Pro Ile Thr
    610                 615                 620

Glu Met Ile Glu Tyr Leu Pro Glu Cys Met Lys Val Leu Leu Asp Phe
625                 630                 635                 640

Cys Met Leu His Ser Thr Glu Asp Lys Ser Cys Arg Asp Tyr Tyr Ile
                645                 650                 655

Glu Tyr Asn Phe Lys Tyr Leu Gln Cys Pro Leu Glu Phe Thr Lys Lys
            660                 665                 670

Thr Pro Thr Gln Asp Val Ile Tyr Glu Pro Leu Thr Ala Leu Asn Ala
            675                 680                 685

Met Val Gln Asn Asn Arg Ile Glu Leu Leu Asn His Pro Val Cys Lys
        690                 695                 700

Glu Tyr Leu Leu Met Lys Trp Leu Ala Tyr Gly Phe Arg Ala His Met
705                 710                 715                 720

Met Asn Leu Gly Ser Tyr Cys Leu Gly Leu Ile Pro Met Thr Ile Leu
                725                 730                 735

Val Val Asn Ile Lys Pro Gly Met Ala Phe Asn Ser Thr Gly Ile Ile
            740                 745                 750

Asn Glu Thr Ser Asp His Ser Glu Ile Leu Asp Thr Thr Asn Ser Tyr
            755                 760                 765

Leu Ile Lys Thr Cys Met Ile Leu Val Phe Leu Ser Ser Ile Phe Gly
    770                 775                 780

Tyr Cys Lys Glu Ala Gly Gln Ile Phe Gln Gln Lys Arg Asn Tyr Phe
```

```
                785                 790                 795                 800
Met Asp Ile Ser Asn Val Leu Glu Trp Ile Ile Tyr Thr Thr Gly Ile
                    805                 810                 815

Ile Phe Val Leu Pro Leu Phe Val Glu Ile Pro Ala His Leu Gln Trp
                820                 825                 830

Gln Cys Gly Ala Ile Ala Val Tyr Phe Tyr Trp Met Asn Phe Leu Leu
                835                 840                 845

Tyr Leu Gln Arg Phe Glu Asn Cys Gly Ile Phe Ile Val Met Leu Glu
                850                 855                 860

Val Ile Leu Lys Thr Leu Leu Arg Ser Thr Val Val Phe Ile Phe Leu
865                 870                 875                 880

Leu Leu Ala Phe Gly Leu Ser Phe Tyr Ile Leu Leu Asn Leu Gln Asp
                    885                 890                 895

Pro Phe Ser Ser Pro Leu Leu Ser Ile Ile Gln Thr Phe Ser Met Met
                900                 905                 910

Leu Gly Asp Ile Asn Tyr Arg Glu Ser Phe Leu Glu Pro Tyr Leu Arg
                    915                 920                 925

Asn Glu Leu Ala His Pro Val Leu Ser Phe Ala Gln Leu Val Ser Phe
930                 935                 940

Thr Ile Phe Val Pro Ile Val Leu Met Asn Leu Leu Ile Gly Leu Ala
945                 950                 955                 960

Val Gly Asp Ile Ala Glu Val Gln Lys His Ala Ser Leu Lys Arg Ile
                    965                 970                 975

Ala Met Gln Val Glu Leu His Thr Ser Leu Glu Lys Lys Leu Pro Leu
                980                 985                 990

Trp Phe Leu Arg Lys Val Asp Gln Lys Ser Thr Ile Val Tyr Pro Asn
                995                 1000                1005

Lys Pro Arg Ser Gly Gly Met Leu Phe His Ile Phe Cys Phe Leu Phe
                1010                1015                1020

Cys Thr Gly Glu Ile Arg Gln Glu Ile Pro Asn Ala Asp Lys Ser Leu
1025                1030                1035                1040

Glu Met Glu Ile Leu Lys Gln Lys Tyr Arg Leu Lys Asp Leu Thr Phe
                1045                1050                1055

Leu Leu Glu Lys Gln His Glu Leu Ile Lys Leu Ile Ile Gln Lys Met
                1060                1065                1070

Glu Ile Ile Ser Glu Thr Glu Asp Asp Ser His Cys Ser Phe Gln
                1075                1080                1085

Asp Arg Phe Lys Lys Glu Gln Met Glu Gln Arg Asn Ser Arg Trp Asn
                1090                1095                1100

Thr Val Leu Arg Ala Val Lys Ala Lys Thr His His Leu Glu Pro
1105                1110                1115

<210> SEQ ID NO 2
<211> LENGTH: 3360
<212> TYPE: DNA
<213> ORGANISM: Homo sapiens

<400> SEQUENCE: 2
atgaagcgca gcctgaggaa gatgtggcgc cctggagaaa agaaggagcc ccagggcgtt    60
gtctatgagg atgtgccgga cgacacggag gatttcaagg aatcgcttaa ggtggttttt   120
gaaggaagtg catatggatt acaaaacttt aataagcaaa agaaattaaa agatgtgac    180 gatatggaca ccttcttctt gcattatgct gcagcagaag ccaaattga ctaatggag     240 aagatcacca gagattcctc tttggaagtg ctgcatgaaa tggatgatta tggaaatacc   300
```

```
cctctgcatt gtgctgtaga aaaaaaccaa attgaaagcg ttaagtttct tctcagcaga    360
ggagcaaacc caaacctccg aaacttcaac atgatggctc ctctccacat agctgtgcag    420
ggcatgaata atgaggtgat gaaggtcttg ctttgagcata gaactattga tgttaatttg    480
gaaggagaaa atggaaacac agctgtgatc attgcgtgca ccacaaataa tagcgaagca    540
ttgcagattt tgcttaacaa aggagctaag ccatgtaaat caaataaatg gggatgtttc    600
cctattcacc aagctgcatt ttcaggttcc aaagaatgca tggaaataat actaaggttt    660
ggtgaagagc atgggtacag tagacagttg cacattaact ttatgaataa tgggaaagcc    720 accccctctcc acctggctgt gcaaaatggt gacttggaaa tgatcaaaat gtgcctggac    780
aatggtgcac aaatagaccc agtggagaag ggaaggtgca cagccattca ttttgctgcc    840
acccagggag ccactgagat tgttaaactg atgatatcgt cctattctgg tagcgtggat    900
attgttaaca caaccgatgg atgtcatgag accatgcttc acagagcttc attgtttgat    960
caccatgagc tagcagacta tttaatttca gtgggagcag atattaataa gatcgattct   1020
gaaggacgct ctccacttat attagcaact gcttctgcat cttggaatat tgtaaatttg   1080
ctactctcta aaggtgccca agtagacata aaagataatt ttggacgtaa ttttctgcat   1140
ttaactgtac agcaacctta tggattaaaa aatctgcgac ctgaatttat gcagatgcaa   1200
cagatcaaag agctggtaat ggatgaagac aacgatgggt gtactcctct acattatgca   1260
tgtagacagg ggggccctgg ttctgtaaat aacctacttg gctttaatgt gtccattcat   1320
tccaaaagca agataagaa atcacctctg cattttgcag ccagttatgg gcgtatcaat   1380
acctgtcaga ggctcctaca agacataagt gatacgaggc ttctgaatga aggtgacctt   1440 catgaatga ctcctctcca tctggcagca aagaatggac atgataaagt agttcagctt   1500
cttctgaaaa aaggtgcatt gtttctcagt gaccacaatg gctggacagc tttgcatcat   1560
gcgtccatgg gcgggtacac tcagaccatg aaggtcattc ttgatactaa tttgaagtgc   1620
acagatcgct tggatgaaga cgggaacact gcacttcact ttgctgcaag ggaaggccat   1680
gccaaagccg ttgcgcttct tctgagccac aatgctgaca tagtcctgaa caagcagcag   1740
gcctcctttt tgcaccttgc acttcacaat aagaggaagg aggttgttct tacgatcatc   1800
aggagcaaaa gatgggatga atgtcttaag atttttcagtc ataattctcc aggcaataaa   1860
tgtccaatta cagaaatgat agaatacctc cctgaatgca tgaaggtact tttagatttc   1920
tgcatgttgc attccacaga agacaagtcc tgccgagact attatatcga gtataatttc   1980
aaatatcttc aatgtccatt agaattcacc aaaaaaacac ctacacagga tgttatatat   2040
gaaccgctta cagccctcaa cgcaatggta caaaataacc gcatagagct tctcaatcat   2100
cctgtgtgta aagaatattt actcatgaaa tggttggctt atggatttag agctcatatg   2160
atgaatttag gatcttactg tcttggtctc ataccttatga ccattctcgt tgtcaatata   2220
aaaccaggaa tggctttcaa ctcaactggc atcatcaatg aaactagtga tcattcagaa   2280
atactagata ccacgaattc atatctaata aaaacttgta tgattttagt gttttatcta   2340
agtatatttg ggtattgcaa agaagcgggg caaattttcc aacagaaaag gaattatttt   2400
atggatataa gcaatgttct tgaatggatt atctacacga cgggcatcat ttttgtgctg   2460 ccccttgtttg ttgaaatacc agctcatctg cagtggcaat gtggagcaat tgctgtttac   2520
ttctattgga tgaatttctt attgtatctt caaagatttg aaaattgtgg aatttttatt   2580
gttatgttgg aggtaatttt gaaaactttg ttgaggtcta cagttgtatt tatcttcctt   2640
```

| | | | |
|---|---|---|---|
| cttctggctt ttggactcag cttttacatc ctcctgaatt tacaggatcc cttcagctct | 2700 |
| ccattgcttt ctataatcca gaccttcagc atgatgctag gagatatcaa ttatcgagag | 2760 |
| tccttcctag aaccatatct gagaaatgaa ttggcacatc cagttctgtc ctttgcacaa | 2820 |
| cttgtttcct tcacaatatt tgtcccaatt gtcctcatga atttacttat tggtttggca | 2880 |
| gttggcgaca ttgctgaggt ccagaaacat gcatcattga agaggatagc tatgcaggtg | 2940 |
| gaacttcata ccagcttaga gaagaagctg ccactttggt ttctacgcaa agtggatcag | 3000 |
| aaatccacca tcgtgtatcc aacaaaccc agatctggtg ggatgttatt ccatatattc | 3060 |
| tgttttttat tttgcactgg ggaaataaga caagaaatac caaatgctga taaatcttta | 3120 |
| gaaatggaaa tattaaagca gaaataccgg ctgaaggatc ttacttttct cctggaaaaa | 3180 |
| cagcatgagc tcattaaact gatcattcag aagatggaga tcatctctga cacagaggat | 3240 |
| gatgatagcc attgttcttt tcaagacagg tttaagaaag agcagatgga acaaaggaat | 3300 |
| agcagatgga atactgtgtt gagagcagtc aaggcaaaaa cacaccatct tgagccttag | 3360 |

<210> SEQ ID NO 3
<211> LENGTH: 1119
<212> TYPE: PRT
<213> ORGANISM: Homo sapiens

<400> SEQUENCE: 3

```
Met Lys Cys Ser Leu Arg Lys Met Trp Arg Pro Gly Glu Lys Lys Glu
 1               5                  10                  15

Pro Gln Gly Val Val Tyr Glu Asp Val Pro Asp Asp Thr Glu Asp Phe
             20                  25                  30

Lys Glu Ser Leu Lys Val Val Phe Glu Gly Ser Ala Tyr Gly Leu Gln
         35                  40                  45

Asn Phe Asn Lys Gln Lys Lys Leu Lys Thr Cys Asp Asp Met Asp Thr
     50                  55                  60

Phe Phe Leu His Tyr Ala Ala Ala Glu Gly Gln Ile Glu Leu Met Glu
 65                  70                  75                  80

Lys Ile Thr Arg Asp Ser Ser Leu Glu Val Leu His Glu Met Asp Asp
                 85                  90                  95

Tyr Gly Asn Thr Pro Leu His Cys Ala Val Glu Lys Asn Gln Ile Glu
            100                 105                 110

Ser Val Lys Phe Leu Leu Ser Arg Gly Ala Asn Pro Asn Leu Arg Asn
        115                 120                 125

Phe Asn Met Met Ala Pro Leu His Ile Ala Val Gln Gly Met Asn Asn
    130                 135                 140

Glu Val Met Lys Val Leu Leu Glu His Arg Thr Ile Asp Val Asn Leu
145                 150                 155                 160

Glu Gly Glu Asn Gly Asn Thr Ala Val Ile Ile Ala Cys Thr Thr Asn
                165                 170                 175

Asn Ser Glu Ala Leu Gln Ile Leu Leu Asn Lys Gly Ala Lys Pro Cys
            180                 185                 190

Lys Ser Asn Lys Trp Gly Cys Phe Pro Ile His Gln Ala Ala Phe Ser
        195                 200                 205

Gly Ser Lys Glu Cys Met Glu Ile Ile Leu Arg Phe Gly Glu Glu His
    210                 215                 220

Gly Tyr Ser Arg Gln Leu His Ile Asn Phe Met Asn Asn Gly Lys Ala
225                 230                 235                 240

Thr Pro Leu His Leu Ala Val Gln Asn Gly Asp Leu Glu Met Ile Lys
                245                 250                 255
```

```
Met Cys Leu Asp Asn Gly Ala Gln Ile Asp Pro Val Glu Lys Gly Arg
            260                 265                 270
Cys Thr Ala Ile His Phe Ala Thr Gln Gly Ala Thr Glu Ile Val
        275                 280                 285
Lys Leu Met Ile Ser Ser Tyr Ser Gly Ser Val Asp Ile Val Asn Thr
        290                 295                 300
Thr Asp Gly Cys His Glu Thr Met Leu His Arg Ala Ser Leu Phe Asp
305                 310                 315                 320
His His Glu Leu Ala Asp Tyr Leu Ile Ser Val Gly Ala Asp Ile Asn
                325                 330                 335
Lys Ile Asp Ser Glu Gly Arg Ser Pro Leu Ile Leu Ala Thr Ala Ser
            340                 345                 350
Ala Ser Trp Asn Ile Val Asn Leu Leu Leu Ser Lys Gly Ala Gln Val
            355                 360                 365
Asp Ile Lys Asp Asn Phe Gly Arg Asn Phe Leu His Leu Thr Val Gln
        370                 375                 380
Gln Pro Tyr Gly Leu Lys Asn Leu Arg Pro Glu Phe Met Gln Met Gln
385                 390                 395                 400
Gln Ile Lys Glu Leu Val Met Asp Glu Asp Asn Asp Gly Cys Thr Pro
                405                 410                 415
Leu His Tyr Ala Cys Arg Gln Gly Gly Pro Gly Ser Val Asn Asn Leu
            420                 425                 430
Leu Gly Phe Asn Val Ser Ile His Ser Lys Ser Lys Asp Lys Lys Ser
            435                 440                 445
Pro Leu His Phe Ala Ala Ser Tyr Gly Arg Ile Asn Thr Cys Gln Arg
        450                 455                 460
Leu Leu Gln Asp Ile Ser Asp Thr Arg Leu Leu Asn Glu Gly Asp Leu
465                 470                 475                 480
His Gly Met Thr Pro Leu His Leu Ala Ala Lys Asn Gly His Asp Lys
                485                 490                 495
Val Val Gln Leu Leu Leu Lys Lys Gly Ala Leu Phe Leu Ser Asp His
            500                 505                 510
Asn Gly Trp Thr Ala Leu His His Ala Ser Met Gly Gly Tyr Thr Gln
            515                 520                 525
Thr Met Lys Val Ile Leu Asp Thr Asn Leu Lys Cys Thr Asp Arg Leu
        530                 535                 540
Asp Glu Asp Gly Asn Thr Ala Leu His Phe Ala Ala Arg Glu Gly His
545                 550                 555                 560
Ala Lys Ala Val Ala Leu Leu Leu Ser His Asn Ala Asp Ile Val Leu
                565                 570                 575
Asn Lys Gln Gln Ala Ser Phe Leu His Leu Ala Leu His Asn Lys Arg
            580                 585                 590
Lys Glu Val Val Leu Thr Ile Ile Arg Ser Lys Arg Trp Asp Glu Cys
            595                 600                 605
Leu Lys Ile Phe Ser His Asn Ser Pro Gly Asn Lys Cys Pro Ile Thr
        610                 615                 620
Glu Met Ile Glu Tyr Leu Pro Glu Cys Met Lys Val Leu Leu Asp Phe
625                 630                 635                 640
Cys Met Leu His Ser Thr Glu Asp Lys Ser Cys Arg Asp Tyr Tyr Ile
                645                 650                 655
Glu Tyr Asn Phe Lys Tyr Leu Gln Cys Pro Leu Glu Phe Thr Lys Lys
            660                 665                 670
```

-continued

Thr Pro Thr Gln Asp Val Ile Tyr Glu Pro Leu Thr Ala Leu Asn Ala
        675                 680                 685

Met Val Gln Asn Asn Arg Ile Glu Leu Leu Asn His Pro Val Cys Lys
690                 695                 700

Glu Tyr Leu Leu Met Lys Trp Leu Ala Tyr Gly Phe Arg Ala His Met
705                 710                 715                 720

Met Asn Leu Gly Ser Tyr Cys Leu Gly Leu Ile Pro Met Thr Ile Leu
                725                 730                 735

Val Val Asn Ile Lys Pro Gly Met Ala Phe Asn Ser Thr Gly Ile Ile
            740                 745                 750

Asn Glu Thr Ser Asp His Ser Glu Ile Leu Asp Thr Thr Asn Ser Tyr
        755                 760                 765

Leu Ile Lys Thr Cys Met Ile Leu Val Phe Leu Ser Ser Ile Phe Gly
    770                 775                 780

Tyr Cys Lys Glu Ala Gly Gln Ile Phe Gln Gln Lys Arg Asn Tyr Phe
785                 790                 795                 800

Met Asp Ile Ser Asn Val Leu Glu Trp Ile Ile Tyr Thr Thr Gly Ile
                805                 810                 815

Ile Phe Val Leu Pro Leu Phe Val Glu Ile Pro Ala His Leu Gln Trp
            820                 825                 830

Gln Cys Gly Ala Ile Ala Val Tyr Phe Tyr Trp Met Asn Phe Leu Leu
        835                 840                 845

Tyr Leu Gln Arg Phe Glu Asn Cys Gly Ile Phe Ile Val Met Leu Glu
    850                 855                 860

Val Ile Leu Lys Thr Leu Leu Arg Ser Thr Val Val Phe Ile Phe Leu
865                 870                 875                 880

Leu Leu Ala Phe Gly Leu Ser Phe Tyr Ile Leu Leu Asn Leu Gln Asp
                885                 890                 895

Pro Phe Ser Ser Pro Leu Leu Ser Ile Ile Gln Thr Phe Ser Met Met
            900                 905                 910

Leu Gly Asp Ile Asn Tyr Arg Glu Ser Phe Leu Glu Pro Tyr Leu Arg
        915                 920                 925

Asn Glu Leu Ala His Pro Val Leu Ser Phe Ala Gln Leu Val Ser Phe
    930                 935                 940

Thr Ile Phe Val Pro Ile Val Leu Met Asn Leu Leu Ile Gly Leu Ala
945                 950                 955                 960

Val Gly Asp Ile Ala Glu Val Gln Lys His Ala Ser Leu Lys Arg Ile
                965                 970                 975

Ala Met Gln Val Glu Leu His Thr Ser Leu Glu Lys Lys Leu Pro Leu
            980                 985                 990

Trp Phe Leu Arg Lys Val Asp Gln Lys Ser Thr Ile Val Tyr Pro Asn
        995                 1000                1005

Lys Pro Arg Ser Gly Gly Met Leu Phe His Ile Phe Cys Phe Leu Phe
    1010                1015                1020

Cys Thr Gly Glu Ile Arg Gln Glu Ile Pro Asn Ala Asp Lys Ser Leu
1025                1030                1035                1040

Glu Met Glu Ile Leu Lys Gln Lys Tyr Arg Leu Lys Asp Leu Thr Phe
                1045                1050                1055

Leu Leu Glu Lys Gln His Glu Leu Ile Lys Leu Ile Ile Gln Lys Met
            1060                1065                1070

Glu Ile Ile Ser Glu Thr Glu Asp Asp Ser His Cys Ser Phe Gln
        1075                1080                1085

Asp Arg Phe Lys Lys Glu Gln Met Glu Gln Arg Asn Ser Arg Trp Asn

Thr Val Leu Arg Ala Val Lys Ala Lys Thr His His Leu Glu Pro
1105            1110            1115

<210> SEQ ID NO 4
<211> LENGTH: 3360
<212> TYPE: DNA
<213> ORGANISM: Homo sapiens

<400> SEQUENCE: 4

| | | | | | |
|---|---|---|---|---|---|
| atgaagtgca | gcctgaggaa | gatgtggcgc | cctggagaaa | agaaggagcc | ccagggcgtt | 60 |
| gtctatgagg | atgtgccgga | cgacacggag | gatttcaagg | aatcgcttaa | ggtggttttt | 120 |
| gaaggaagtg | catatggatt | acaaaacttt | aataagcaaa | agaaattaaa | aacatgtgac | 180 |
| gatatggaca | ccttcttctt | gcattatgct | gcagcagaag | gccaaattga | gctaatggag | 240 |
| aagatcacca | gagattcctc | tttggaagtg | ctgcatgaaa | tggatgatta | tggaaatacc | 300 |
| cctctgcatt | gtgctgtaga | aaaaaaccaa | attgaaagcg | ttaagttcct | tctcagcaga | 360 |
| ggagcaaacc | caaacctccg | aaacttcaac | atgatggctc | ctctccacat | agctgtgcag | 420 |
| ggcatgaata | atgaggtgat | gaaggtcttg | cttgagcata | gaactattga | tgttaatttg | 480 |
| gaaggagaaa | atggaaacac | agctgtgatc | attgcgtgca | ccacaaataa | tagcgaagca | 540 |
| ttgcagattt | tgcttaacaa | aggagctaag | ccatgtaaat | caaataaatg | gggatgtttc | 600 |
| cctattcacc | aagctgcatt | ttcaggttcc | aaagaatgca | tggaaataat | actaaggttt | 660 |
| ggtgaagagc | atgggtacag | tagacagttg | cacattaact | ttatgaataa | tgggaaagcc | 720 |
| accctctcc | acctggctgt | gcaaaatggt | gacttggaaa | tgatcaaaat | gtgcctggac | 780 |
| aatggtgcac | aaatagaccc | agtggagaag | ggaaggtgca | cagccattca | ttttgctgcc | 840 |
| acccagggag | ccactgagat | tgttaaactg | atgatatcgt | cctattctgg | tagcgtggat | 900 |
| attgttaaca | caaccgatgg | atgtcatgag | accatgcttc | acagagcttc | attgtttgat | 960 |
| caccatgagc | tagcagacta | tttaatttca | gtgggagcag | atattaataa | gatcgattct | 1020 |
| gaaggacgct | ctccacttat | attagcaact | gcttctgcat | cttggaatat | tgtaaatttg | 1080 |
| ctactctcta | aagtgcccca | agtagacata | aaagataatt | ttggacgtaa | ttttctgcat | 1140 |
| ttaactgtac | agcaacctta | tggattaaaa | aatctgcgac | ctgaatttat | gcagatgcaa | 1200 |
| cagatcaaag | agctggtaat | ggatgaagac | aacgatgggt | gtactcctct | acattatgca | 1260 |
| tgtagacagg | ggggccctgg | ttctgtaaat | aacctacttg | gctttaatgt | gtccattcat | 1320 |
| tccaaaagca | aagataagaa | atcacctctg | cattttgcag | ccagttatgg | gcgtatcaat | 1380 |
| acctgtcaga | ggctcctaca | agacataagt | gatacgaggc | ttctgaatga | aggtgacctt | 1440 |
| catgaatga | ctcctctcca | tctggcagca | agaatggac | atgataaagt | agttcagctt | 1500 |
| cttctgaaaa | aaggtgcatt | gtttctcagt | gaccacaatg | gctggacagc | tttgcatcat | 1560 |
| gcgtccatgg | gcgggtacac | tcagaccatg | aaggtcattc | ttgatactaa | tttgaagtgc | 1620 |
| acagatcgct | tggatgaaga | cgggaacact | gcacttcact | ttgctgcaag | ggaaggccac | 1680 |
| gccaaagccg | ttgcgcttct | tctgagccac | aatgctgaca | tagtcctgaa | caagcagcag | 1740 |
| gcctcctttt | tgcaccttgc | acttcacaat | aagaggaagg | aggttgttct | tacgatcatc | 1800 |
| aggagcaaaa | gatgggatga | atgtcttaag | attttcagtc | ataattctcc | aggcaataaa | 1860 |
| tgtccaatta | cagaaatgat | agaataccctc | cctgaatgca | tgaaggtact | tttagatttc | 1920 |
| tgcatgttgc | attccacaga | agacaagtcc | tgccgagact | attatcga | gtataatttc | 1980 |

```
aaatatcttc aatgtccatt agaattcacc aaaaaaacac ctacacagga tgttatatat    2040
gaaccgctta cagccctcaa cgcaatggta caaataacc gcatagagct tctcaatcat     2100
cctgtgtgta aagaatattt actcatgaaa tggttggctt atggatttag agctcatatg   2160
atgaatttag gatcttactg tcttggtctc ataccatga ccattctcgt tgtcaatata    2220
aaaccaggaa tggctttcaa ctcaactggc atcatcaatg aaactagtga tcattcagaa   2280
atactagata ccacgaattc atatctaata aaaacttgta tgattttagt gtttttatca   2340
agtatatttg ggtattgcaa agaagcgggg caaattttcc aacagaaaag gaattatttt   2400
atggatataa gcaatgttct tgaatggatt atctacacga cgggcatcat ttttgtgctg   2460
cccttgtttg ttgaaatacc agctcatctg cagtggcaat gtggagcaat tgctgtttac   2520
ttctattgga tgaatttctt attgtatctt caaagatttg aaaattgtgg aattttatt    2580 gttatgttgg aggtaatttt gaaaactttg ttgaggtcta cagttgtatt tatcttcctt   2640
cttctggctt ttggactcag cttttacatc ctcctgaatt tacaggatcc cttcagctct   2700
ccattgcttt ctataatcca gaccttcagc atgatgctag gagatatcaa ttatcgagag   2760
tccttcctag aaccatatct gagaaatgaa ttggcacatc cagttctgtc ctttgcacaa   2820
cttgtttcct tcacaatatt tgtcccaatt gtcctcatga atttacttat tggtttggca   2880
gttggcgaca ttgctgaggt ccagaaacat gcatcattga agaggatagc tatgcaggtg   2940
gaacttcata ccagcttaga gaagaagctg ccactttggt ttctacgcaa agtggatcag   3000
aaatccacca tcgtgtatcc caacaaaccc agatctggtg ggatgttatt ccatatattc   3060 tgtttttttat tttgcactgg ggaaataaga caagaaatac caaatgctga taaatctta   3120 gaaatggaaa tattaaagca gaaataccgg ctgaaggatc ttacttttct cctggaaaaa   3180
cagcatgagc tcattaaact gatcattcag aagatggaga tcatctctga cagagggat   3240 gatgatagcc attgttcttt tcaagacagg tttaagaaag agcagatgga acaaaggaat  3300
agcagatgga atactgtgtt gagagcagtc aaggcaaaaa cacaccatct tgagccttag  3360
```

<210> SEQ ID NO 5
<211> LENGTH: 1125
<212> TYPE: PRT
<213> ORGANISM: mus musculus

<400> SEQUENCE: 5

```
Met Lys Arg Gly Leu Arg Arg Ile Leu Leu Pro Glu Glu Arg Lys Glu
1               5                   10                  15

Val Gln Gly Val Val Tyr Arg Gly Val Gly Glu Asp Met Asp Cys Ser
            20                  25                  30

Lys Glu Ser Phe Lys Val Asp Ile Glu Gly Asp Met Cys Arg Leu Glu
        35                  40                  45

Asp Phe Ile Lys Asn Arg Arg Lys Leu Ser Lys Tyr Glu Asp Glu Asn
    50                  55                  60

Leu Cys Pro Leu His His Ala Ala Ala Glu Gly Gln Val Glu Leu Met
65                  70                  75                  80

Glu Leu Ile Ile Asn Gly Ser Ser Cys Glu Val Leu Asn Ile Met Asp
                85                  90                  95

Gly Tyr Gly Asn Thr Pro Leu His Cys Ala Ala Glu Lys Asn Gln Val
            100                 105                 110

Glu Ser Val Lys Phe Leu Leu Ser Gln Gly Ala Asn Pro Asn Leu Arg
        115                 120                 125

Asn Arg Asn Met Met Ser Pro Leu His Ile Ala Val His Gly Met Tyr
```

```
                130                 135                 140
Asn Glu Val Ile Lys Val Leu Thr Glu His Lys Ala Thr Asn Ile Asn
145                 150                 155                 160

Leu Glu Gly Glu Asn Gly Asn Thr Ala Leu Met Ser Thr Cys Ala Lys
                165                 170                 175

Asp Asn Ser Glu Ala Leu Gln Ile Leu Leu Glu Lys Gly Ala Lys Leu
                180                 185                 190

Cys Lys Ser Asn Lys Trp Gly Asp Tyr Pro Val His Gln Ala Ala Phe
                195                 200                 205

Ser Gly Ala Lys Lys Cys Met Glu Leu Ile Leu Ala Tyr Gly Glu Lys
        210                 215                 220

Asn Gly Tyr Ser Arg Glu Thr His Ile Asn Phe Val Asn His Lys Lys
225                 230                 235                 240

Ala Ser Pro Leu His Leu Ala Val Gln Ser Gly Asp Leu Asp Met Ile
                245                 250                 255

Lys Met Cys Leu Asp Asn Gly Ala His Ile Asp Met Met Glu Asn Ala
                260                 265                 270

Lys Cys Met Ala Leu His Phe Ala Ala Thr Gln Gly Ala Thr Asp Ile
                275                 280                 285

Val Lys Leu Met Ile Ser Ser Tyr Thr Gly Ser Ser Asp Ile Val Asn
        290                 295                 300

Ala Val Asp Gly Asn Gln Glu Thr Leu Leu His Arg Ala Ser Leu Phe
305                 310                 315                 320

Asp His His Asp Leu Ala Glu Tyr Leu Ile Ser Val Gly Ala Asp Ile
                325                 330                 335

Asn Ser Thr Asp Ser Glu Gly Arg Ser Pro Leu Ile Leu Ala Thr Ala
                340                 345                 350

Ser Ala Ser Trp Asn Ile Val Asn Leu Leu Leu Cys Lys Gly Ala Lys
                355                 360                 365

Val Asp Ile Lys Asp His Leu Gly Arg Asn Phe Leu His Leu Thr Val
        370                 375                 380

Gln Gln Pro Tyr Gly Leu Arg Asn Leu Arg Pro Glu Phe Met Gln Met
385                 390                 395                 400

Gln His Ile Lys Glu Leu Val Met Asp Glu Asp Asn Asp Gly Cys Thr
                405                 410                 415

Pro Leu His Tyr Ala Cys Arg Gln Gly Val Pro Val Ser Val Asn Asn
                420                 425                 430

Leu Leu Gly Phe Asn Val Ser Ile His Ser Lys Ser Lys Asp Lys Lys
                435                 440                 445

Ser Pro Leu His Phe Ala Ala Ser Tyr Gly Arg Ile Asn Thr Cys Gln
                450                 455                 460

Arg Leu Leu Gln Asp Ile Ser Asp Thr Arg Leu Leu Asn Glu Gly Asp
465                 470                 475                 480

Leu His Gly Met Thr Pro Leu His Leu Ala Ala Lys Asn Gly His Asp
                485                 490                 495

Lys Val Val Gln Leu Leu Leu Lys Lys Gly Ala Leu Phe Leu Ser Asp
                500                 505                 510

His Asn Gly Trp Thr Ala Leu His His Ala Ser Met Gly Gly Tyr Thr
                515                 520                 525

Gln Thr Met Lys Val Ile Leu Asp Thr Asn Leu Lys Cys Thr Asp Arg
                530                 535                 540

Leu Asp Glu Glu Gly Asn Thr Ala Leu His Phe Ala Ala Arg Glu Gly
545                 550                 555                 560
```

-continued

His Ala Lys Ala Val Ala Met Leu Leu Ser Tyr Asn Ala Asp Ile Leu
                565                 570                 575

Leu Asn Lys Lys Gln Ala Ser Phe Leu His Ile Ala Leu His Asn Lys
                580                 585                 590

Arg Lys Glu Val Val Leu Thr Thr Ile Arg Asn Lys Arg Trp Asp Glu
                595                 600                 605

Cys Leu Gln Val Phe Thr His Asn Ser Pro Ser Asn Arg Cys Pro Ile
        610                 615                 620

Met Glu Met Val Glu Tyr Leu Pro Glu Cys Met Lys Val Leu Leu Asp
625                 630                 635                 640

Phe Cys Met Ile Pro Ser Thr Glu Asp Lys Ser Cys Gln Asp Tyr His
                645                 650                 655

Ile Glu Tyr Asn Phe Lys Tyr Leu Gln Cys Pro Leu Ser Met Thr Lys
                660                 665                 670

Lys Val Ala Pro Thr Gln Asp Val Val Tyr Glu Pro Leu Thr Ile Leu
                675                 680                 685

Asn Val Met Val Gln His Asn Arg Ile Glu Leu Leu Asn His Pro Val
                690                 695                 700

Cys Arg Glu Tyr Leu Leu Met Lys Trp Cys Ala Tyr Gly Phe Arg Ala
705                 710                 715                 720

His Met Met Asn Leu Gly Ser Tyr Cys Leu Gly Leu Ile Pro Met Thr
                725                 730                 735

Leu Leu Val Val Lys Ile Gln Pro Gly Met Ala Phe Asn Ser Thr Gly
                740                 745                 750

Ile Ile Asn Gly Thr Ser Ser Thr His Glu Glu Arg Ile Asp Thr Leu
                755                 760                 765

Asn Ser Phe Pro Ile Lys Ile Cys Met Ile Leu Val Phe Leu Ser Ser
                770                 775                 780

Ile Phe Gly Tyr Cys Lys Glu Val Ile Gln Ile Phe Gln Gln Lys Arg
785                 790                 795                 800

Asn Tyr Phe Leu Asp Tyr Asn Asn Ala Leu Glu Trp Val Ile Tyr Thr
                805                 810                 815

Thr Ser Ile Ile Phe Val Leu Pro Leu Phe Leu Asn Ile Pro Ala Tyr
                820                 825                 830

Met Gln Trp Gln Cys Gly Ala Ile Ala Ile Phe Phe Tyr Trp Met Asn
                835                 840                 845

Phe Leu Leu Tyr Leu Gln Arg Phe Glu Asn Cys Gly Ile Phe Ile Val
                850                 855                 860

Met Leu Glu Val Ile Phe Lys Thr Leu Leu Arg Ser Thr Gly Val Phe
865                 870                 875                 880

Ile Phe Leu Leu Leu Ala Phe Gly Leu Ser Phe Tyr Val Leu Leu Asn
                885                 890                 895

Phe Gln Asp Ala Phe Ser Thr Pro Leu Leu Ser Leu Ile Gln Thr Phe
                900                 905                 910

Ser Met Met Leu Gly Asp Ile Asn Tyr Arg Asp Ala Phe Leu Glu Pro
                915                 920                 925

Leu Phe Arg Asn Glu Leu Ala Tyr Pro Val Leu Thr Phe Gly Gln Leu
                930                 935                 940

Ile Ala Phe Thr Met Phe Val Pro Ile Val Leu Met Asn Leu Leu Ile
945                 950                 955                 960

Gly Leu Ala Val Gly Asp Ile Ala Glu Val Gln Lys His Ala Ser Leu
                965                 970                 975

```
Lys Arg Ile Ala Met Gln Val Glu Leu His Thr Asn Leu Glu Lys Lys
            980                 985                 990

Leu Pro Leu Trp Tyr Leu Arg Lys Val Asp Gln Arg Ser Thr Ile Val
        995                1000                1005

Tyr Pro Asn Arg Pro Arg His Gly Arg Met Leu Arg Phe Phe His Tyr
       1010                1015                1020

Phe Leu Asn Met Gln Glu Thr Arg Gln Glu Val Pro Asn Ile Asp Thr
1025                1030                1035                1040

Cys Leu Glu Met Glu Ile Leu Lys Gln Lys Tyr Arg Leu Lys Asp Leu
                1045                1050                1055

Thr Ser Leu Leu Glu Lys Gln His Glu Leu Ile Lys Leu Ile Ile Gln
            1060                1065                1070

Lys Met Glu Ile Ile Ser Glu Thr Gly Asp Glu Asp Asn His Cys Ser
        1075                1080                1085

Phe Gln Asp Arg Phe Lys Lys Glu Arg Leu Glu Gln Met His Ser Lys
1090                1095                1100

Trp Asn Phe Val Leu Asn Ala Val Lys Thr Lys Thr His Cys Ser Ile
1105                1110                1115                1120

Ser His Pro Asp Phe
            1125

<210> SEQ ID NO 6
<211> LENGTH: 3378
<212> TYPE: DNA
<213> ORGANISM: mus musculus

<400> SEQUENCE: 6
atgaagcgcg gcttgaggag gattctgctc ccggaggaaa ggaaggaggt ccagggcgtt      60
gtctatcgcg cgtcgggga  agacatggac tgctccaagg aatcctttaa ggtggacatt     120
gaaggagata tgtgtagatt agaagacttc atcaagaacc gaagaaaact aagcaaatat     180
gaggatgaaa atctctgtcc tctgcatcac gcagcagcag aaggtcaagt tgaactgatg     240
gaactgatca tcaatggttc ttcgtgtgaa gtgctgaata atggatgg ttatggaaat       300 accccactgc attgtgctgc agaaaaaaat caagttgaaa gtgtaaagtt tcttctcagc     360
caaggagcaa atccaaacct ccgaaataga acatgatgt caccccttca catagctgtg      420
catggcatgt acaacgaagt gatcaaggtg ttgactgagc acaaggccac taacatcaat     480
ttagaaggag agaatgggaa cacggctttg atgtccacgt gtgccaaaga caacagtgaa     540
gctttgcaaa ttttgttaga aaaggagct aagctgtgta atcaaataa gtggggagac       600 taccctgtgc accaggcagc attttcaggt gccaaaaaat gcatggaatt aatcttagca     660
tatggtgaaa agaacggcta cagcagggag actcacatta attttgtgaa tcacaagaaa     720
gccagccctc tccacctagc agttcaaagc ggagacttgg acatgattaa gatgtgcctg     780
gacaacggtg cacacatcga catgatggag aatgccaaat gcatggccct ccatttttgct    840 gcaacccagg gagccactga catcgttaag ctcatgatct catcctatac cggaagtagt     900
gatattgtga atgcagttga tgcaatcag gagaccctgc ttcacagagc ctcgttattt      960
gatcaccatg acctggcaga atacctaata tcagtgggag cagacatcaa cagcactgat    1020
tctgaaggac gctctccact tattttagca acagcttctg catcctggaa cattgtgaat    1080
ttgctcctct gtaaaggtgc caaagtagac ataaagatc atcttggacg taactttttg     1140
catttgactg tgcagcagcc ttatggacta agaaatttgc ggcctgagtt tatgcagatg    1200
caacacatca aagagctggt gatggatgaa gacaatgacg gatgcacacc tctccattat    1260
```

-continued

```
gcctgtaggc aggggggttcc tgtctctgta ataaccctcc ttggcttcaa tgtgtccatt    1320
catagcaaaa gtaaagataa gaagtcgccc ctgcattttg cagccagtta tgggcgcatc    1380
aatacatgtc agagacttct gcaagacata agtgatacga ggcttttgaa tgaaggggat    1440
ctccatggga tgacccctct ccacctggca gcaaaaaatg ggcatgataa agtcgttcaa    1500
ctccttctga agaaggggc cttatttctc agtgaccaca atggctggac tgctttgcat     1560
cacgcctcca tgggtgggta cactcagacc atgaaggtca ttcttgatac taacttgaaa    1620
tgcacagacc gactagatga agaagggaac acagcactcc actttgcagc acgggaaggc    1680
catgccaagg ctgttgcaat gcttttgagc tacaatgctg acatcctcct gaacaagaag    1740
caagcttcct ttctgcatat tgccctgcac aataagcgca aggaagtggt tctcacaacc    1800
atcagaaata aagatgggga tgagtgtctt caagttttca ctcataattc tccaagcaat    1860
cgatgtccaa tcatggagat ggtagaatac ctccccgagt gcatgaaagt tcttttagat    1920
ttctgcatga taccttccac agaagacaag tcctgtcaag actaccatat tgagtataat    1980
ttcaagtatc tccaatgccc attatccatg accaaaaaag tagcacctac ccaggatgtg    2040
gtatatgagc tcttacaat cctcaatgtc atggtccaac ataaccgcat agaactcctc     2100
aaccaccctg tgtgtaggga gtacttactc atgaaatggt gtgcctatgg attcagggcc    2160
catatgatga acctaggatc ttattgtctt ggtctcatac ccatgaccct tcttgttgtc    2220
aaaatacagc ctggaatggc cttcaattct actggaataa tcaatggaac tagtagtact    2280
catgaggaaa gaatagacac tctgaattca tttccaataa aaatatgtat gattctagtt    2340
tttttatcaa gtatatttgg atattgcaaa gaagtgatcc aaatttttcca acagaaaagg   2400 aattacttcc tggattacaa caatgctctg gaatgggtta tctatacaac tagtatcatc    2460
ttcgtgttgc ccttgttcct caacatccca gcgtatatgc agtggcaatg tggagcaata    2520
gcgatattct tctactggat gaacttccta ctgtatcttc aaaggtttga aactgtgga     2580 atttttcattg ttatgttgga ggtgattttt aaaacattgc tgagatcgac cggagtgttt   2640
atcttcctcc tactggcttt tggcctcagc ttttatgttc tcctgaattt ccaagatgcc    2700
ttcagcaccc cattgctttc cttaatccag acattcagta tgatgctagg agacatcaat    2760
tatcgagatg ccttcctaga accattgttt agaaatgagt tggcataccc agtcctgacc    2820
tttgggcagc ttattgcctt cacaatgttt gtcccaattg ttctcatgaa cttactgatt    2880
ggcttggcgt tggggacat tgctgaggtc cagaagcatg cgtcattgaa gaggattgct    2940
atgcaggtgg aacttcatac caacttagaa aaaaagctgc cactctggta cttacgcaaa    3000
gtggatcaga ggtccaccat cgtgtatcca aatagaccca ggcacggcag gatgctacgg    3060
ttttttcatt actttcttaa tatgcaagaa acacgacaag aagtaccaaa cattgacaca    3120
tgcttggaaa tggaaatatt gaaacagaaa tatcggctga aggacctcac ttccctcttg    3180
gaaaagcagc atgagctcat caaactcatc atccagaaga tggagatcat ctcagagaca    3240
gaagatgaag ataaccattg ctctttccaa gacaggttca agaaggagag gctggaacag    3300
atgcacagca gtggaattt tgtcttaaac gcagttaaga ctaaaacaca ttgttctatt    3360
agccacccgg actttttag                                                3378
```

COMPOUNDS USEFUL FOR TREATING INJURIES FROM WARFARE AGENTS

PRIORITY CLAIM

This application in a continuation of U.S. Ser. No. 12/696,723, filed Jan. 29, 2010, which claims priority to U.S. Ser. No. 61/148,296, filed Jan. 29, 2009, each of which are hereby incorporated by reference in their entirety.

BACKGROUND

The invention relates to compounds and compositions useful for treating disorders related to TRPA1.

A variety of ion channel proteins exist to mediate ion flux across cellular membranes. The proper expression and function of ion channel proteins is essential for the maintenance of cell function and intracellular communication. Numerous diseases are the result of misregulation of membrane potential or aberrant calcium handling. Given the central importance of ion channels in modulating membrane potential and ion flux in cells, identification of agents that can promote or inhibit particular ion channels are of great interest, both as research tools and as therapeutic agents.

SUMMARY OF THE INVENTION

The invention provides compounds, methods and compositions for treating or preventing conditions such as pain by modulating the activity of the TRPA1 channel. The compounds described herein can modulate the function of TRPA1 by inhibiting a TRPA1-mediated ion flux or by inhibiting the inward current, the outward current, or both currents mediated by TRPA1. The inhibition of a particular current is the ability to inhibit or reduce such current (e.g., inward and/or outward) in an in vitro or an in vivo assay. (See Jordt et al. (2004), Nature 427:260-265; Bautista et al., (2005) PNAS: 102(34):12248-12252).

In one aspect, the invention features a method of treating a TRPA1 mediated disorder in a subject. The method includes administering an effective amount of a compound of formula I, or a pharmaceutically acceptable salt thereof:

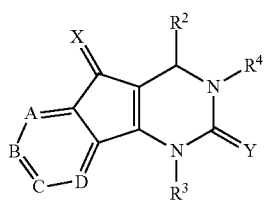

Formula I

Each of A, B, C, and D is $CR^1$ or N, provided that no more than 2 of A, B, C, and D are N; in addition, each of X and Y is, independently, N—R, O or S, where R is H, optionally substituted $C_{1-6}$ alkyl, OH, OR', CN, $NO_2$, or $SO_2R'$, where R' is H or $C_{1-6}$ alkyl; each $R^1$ is, independently, H, optionally substituted $C_{1-6}$ alkyl, optionally substituted $C_{2-6}$ alkenyl, optionally substituted $C_{2-6}$ alkynyl, optionally substituted heterocyclyl, hydroxyl, optionally substituted $C_{1-6}$ alkoxy, optionally substituted $C_{1-6}$ alkenyloxy, cyano, halo, acyl, amino, optionally substituted alkylamino, aminoalkyl, amido, acylamino, alkylurea, alkylcarbamoyl, carboxyl, optionally substituted alkylcarboxyl, thioyl, optionally substituted alkylthio, $SO_3H$, alkylsulfinyl, optionally substituted alkylsulfonyl, or nitro. $R^2$ is optionally substituted cycloalkyl, optionally substituted heterocyclyl, optionally substituted aryl or optionally substituted heteroaryl; each of $R^3$ and $R^4$ is, independently, H, optionally substituted $C_{1-6}$ alkyl, arylalkyl, heteroarylalkyl, alkoxyalkyl, $COR^{10}$, $CO_2R^{10}$, $CH_2CO_2R^{10}$, or $CONHR^{10}$, where $R^{10}$ is H or optionally substituted $C_{1-6}$ alkyl. In some embodiments, at least one of A, B, C, or D is N. For example, in some embodiments, D is N.

In another aspect, the invention features a method of treating pain in a subject. The method includes administering an effective amount of a compound of formula I, or a pharmaceutically acceptable salt thereof:

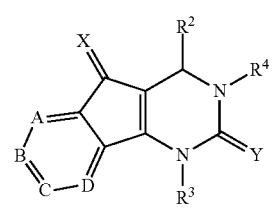

Formula I where the substituents are defined as above. In some embodiments, at least one of A, B, C, or D is N. For example, in some embodiments, D is N.

In another aspect, the invention features a compound having Formula III, or a pharmaceutically acceptable salt thereof:

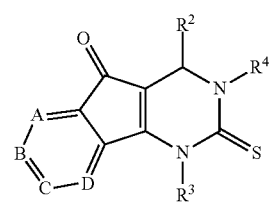

Formula III where each of A, B, C, and D is $CR^1$ or N, provided that no more than 2 of A, B, C, and D are N. In addition, each $R^1$ is, independently, H, optionally substituted $C_{1-6}$ alkyl, optionally substituted $C_{2-6}$ alkenyl, optionally substituted $C_{2-6}$ alkynyl, optionally substituted heterocyclyl, hydroxyl, optionally substituted $C_{1-6}$ alkoxy, $C_{1-6}$ alkenyloxy, cyano, halo, acyl, amino, optionally substituted alkylamino, aminoalkyl, amido, acylamino, alkylurea, alkylcarbamoyl, carboxyl, optionally substituted alkylcarboxyl, thioyl, optionally substituted alkylthio, $SO_3H$, optionally substituted alkylsulfinyl, optionally substituted alkylsulfonyl, or nitro; $R^2$ is optionally substituted cycloalkyl, optionally substituted heterocyclyl, optionally substituted aryl or optionally substituted heteroaryl; and each of $R^3$ and $R^4$ is, independently, H, optionally substituted $C_{1-6}$ alkyl, arylalkyl, heteroarylalkyl, alkoxyalkyl, $COR^{10}$, $CO_2R^{10}$, $CH_2CO_2R^{10}$, or $CONHR^{10}$, where $R^{10}$ is H or optionally substituted $C_{1-6}$ alkyl. However, when A, B, C, and D are all CH, and $R^3$ and $R^4$ are both H, then $R^2$ cannot be 3-nitrophenyl, naphthyl, 2-halophenyl, 3,4,5-trimethoxyphenyl, 2,3-dihydroxyphenyl, unsubstituted phenyl, pyridyl, 4-alkylphenyl, 4-alkoxyphenyl, 4-hydroxyphenyl, 4-halophenyl, 4-nitrophenyl, benzo[1,3]-dioxole. In addition, when A, B, C, and D are all CH and $R^2$ is unsubstituted phenyl or 3,4,5-trimethoxyphenyl, then neither of $R^3$ and $R^4$ can be methyl.

In some embodiments, at least one of A, B, C, or D is N. For example, in some embodiments, D is N. In some embodiments, $R^2$ is optionally substituted phenyl, e.g., meta-substituted phenyl.

In another aspect, the invention features a compound of Formula V, or a pharmaceutically acceptable salt thereof:

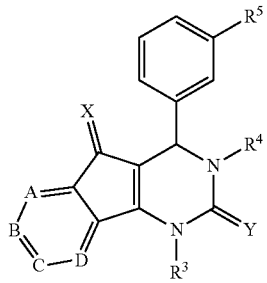

Formula V where each of A, B, C, and D is $CR^1$ or N, provided that no more than 2 of A, B, C, and D are N;
each of X and Y is, independently, N—R, O or S, where R is H, alkyl, OH, OR', CN, $NO_2$, or $SO_2R'$, where R' is H or $C_{1-6}$ alkyl; each $R^1$ is, independently, H, optionally substituted $C_{1-6}$ alkyl, optionally substituted $C_{2-6}$ alkenyl, optionally substituted $C_{2-6}$ alkynyl, optionally substituted heterocyclyl, hydroxyl, optionally substituted $C_{1-6}$ alkoxy, optionally substituted $C_{1-6}$ alkenyloxy, cyano, halo, acyl, amino, optionally substituted alkylamino, aminoalkyl, amido, acylamino, alkylurea, alkylcarbamoyl, carboxyl, optionally substituted alkylcarboxyl, thioyl, optionally substituted alkylthio, $SO_3H$, optionally substituted alkylsulfinyl, optionally substituted alkylsulfonyl, or nitro; each of $R^3$ and $R^4$ is, independently, H, optionally substituted $C_{1-6}$ alkyl, arylalkyl, heteroarylalkyl, alkoxyalkyl, $COR^{10}$, $CO_2R^{10}$, $CH_2CO_2R^{10}$, or $CONHR^{10}$, where $R^{10}$ is H or optionally substituted $C_{1-6}$ alkyl; $R^5$ is hydroxyl, optionally substituted $C_{1-6}$ alkoxy, optionally substituted $C_{1-6}$ alkenyloxy, alkyloxyalkoxy, cyano, acyl, amino, optionally substituted alkylamino, aminoalkyl, amido, acylamino, alkylurea, alkylcarbamoyl, carboxyl, optionally substituted alkylcarboxyl, thioyl, optionally substituted alkylthio, $SO_3H$, optionally substituted alkylsulfinyl, or optionally substituted alkylsulfonyl. In some embodiments, at least one of A, B, C, or D is N. For example, in some embodiments, D is N.

In another aspect, the invention features a compound having Formula VII, or a pharmaceutically acceptable salt thereof:

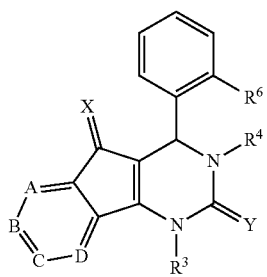

Formula VII where each of A, B, C, and D is $CR^1$ or N, provided that no more than 1 of A, B, C, and D is N;

each of X and Y is, independently, N—R, O or S, where R is H, alkyl, OH, OR', CN, $NO_2$, or $SO_2R'$, where R' is H or $C_{1-6}$ alkyl; each $R^1$ is, independently, H, optionally substituted $C_{1-6}$ alkyl, optionally substituted $C_{2-6}$ alkenyl, optionally substituted $C_{2-6}$ alkynyl, optionally substituted heterocyclyl, hydroxyl, optionally substituted $C_{1-6}$ alkoxy, optionally substituted $C_{1-6}$ alkenyloxy, cyano, halo, acyl, amino, optionally substituted alkylamino, aminoalkyl, amido, acylamino, alkylurea, alkylcarbamoyl, carboxyl, optionally substituted alkylcarboxyl, thioyl, optionally substituted alkylthio, $SO_3H$, optionally substituted alkylsulfinyl, optionally substituted alkylsulfonyl, or nitro; each of $R^3$ and $R^4$ is, independently, H, optionally substituted $C_{1-6}$ alkyl, arylalkyl, heteroarylalkyl, alkoxyalkyl, $COR^{10}$, $CO_2R^{10}$, $CH_2CO_2R^{10}$, or $CONHR^{10}$, where $R^{10}$ is H or optionally substituted $C_{1-6}$ alkyl; $R^6$ is hydroxyl, $C_{1-6}$ alkenyloxy, cyano, acyl, amino, optionally substituted alkylamino, aminoalkyl, amido, acylamino, alkylurea, alkylcarbamoyl, carboxyl, optionally substituted alkylcarboxyl, thioyl, optionally substituted alkylthio, $SO_3H$, optionally substituted alkylsulfinyl, or optionally substituted alkylsulfonyl. In some embodiments, at least one of A, B, C, or D is N. For example, in some embodiments, D is N.

In another aspect, the invention features a compound having Formula VIII, or a pharmaceutically acceptable salt thereof:

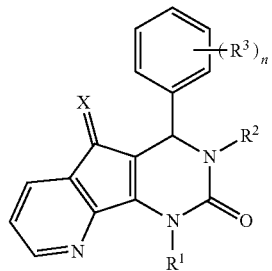

Formula VIII wherein each of $R^1$ and $R^2$ is, independently, H, optionally substituted $C_{1-6}$ alkyl, arylalkyl, heteroarylalkyl, alkoxyalkyl, $COR^{10}$, $CO_2R^{10}$, $CH_2CO_2R^{10}$, or $CONHR^{10}$, where $R^{10}$ is H or optionally substituted $C_{1-6}$ alkyl; and each $R^3$ is, independently, hydroxyl, optionally substituted $C_{1-6}$ alkoxy, optionally substituted $C_{1-6}$ alkenyloxy, alkyloxyalkoxy, cyano, acyl, amino, optionally substituted alkylamino, aminoalkyl, amido, acylamino, alkylurea, alkylcarbamoyl, carboxyl, optionally substituted alkylcarboxyl, thioyl, optionally substituted alkylthio, $SO_3H$, optionally substituted alkylsulfinyl, or optionally substituted alkylsulfonyl; and n is 1-3. In some embodiments, the compound has Formula IX. In other embodiments, the compound has the formula IXa.

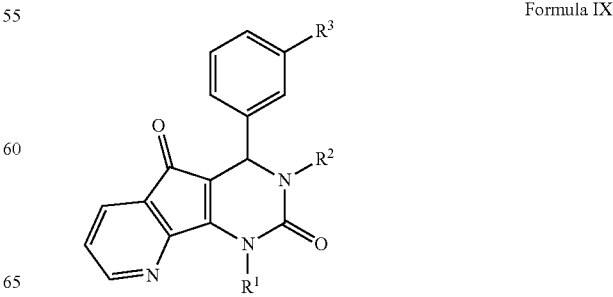

Formula IX

Formula IXa

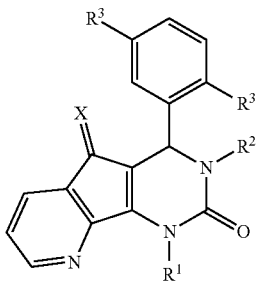

In another embodiment, the invention features a compound having Formula X, or a pharmaceutically acceptable salt thereof:

Formula X

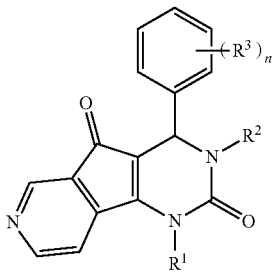

wherein each of $R^1$ and $R^2$ is, independently, H, optionally substituted $C_{1-6}$ alkyl, arylalkyl, heteroarylalkyl, alkoxyalkyl, $COR^{10}$, $CO_2R^{10}$, $CH_2CO_2R^{10}$, or $CONHR^{10}$, where $R^{10}$ is H or optionally substituted $C_{1-6}$ alkyl; each $R^3$ is, independently, hydroxyl, optionally substituted $C_{1-6}$ alkoxy, optionally substituted $C_{1-6}$ alkenyloxy, alkyloxyalkoxy, cyano, acyl, amino, optionally substituted alkylamino, aminoalkyl, amido, acylamino, alkylurea, alkylcarbamoyl, carboxyl, optionally substituted alkylcarboxyl, thioyl, optionally substituted alkylthio, $SO_3H$, optionally substituted alkylsulfinyl, or optionally substituted alkylsulfonyl; and n is 1-3. In some embodiments, the compound has Formula XI. In other embodiments, the compound has Formula XIa.

Formula XI

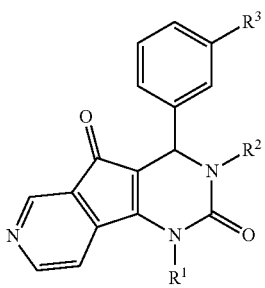

Formula XIa

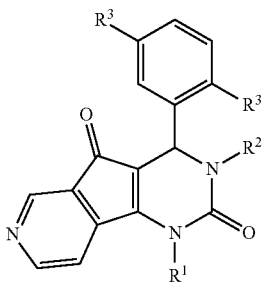

Included within the scope of the invention are, for each compound described herein, the salts thereof, or a solvate, hydrate, oxidative metabolite or prodrug of the compound or its salt. When the compounds are referred to herein, it is understood that salts, solvates, hydrates, oxidative metabolites, and prodrugs of the compounds are also included. Tautomers of the compounds disclosed are also included within the scope of the invention.

Any of the compounds disclosed herein may be used to treat any diseases disclosed herein. In addition, these compounds may be used to inhibit a function of a TRPA1 channel in vitro or in vivo.

DETAILED DESCRIPTION OF THE INVENTION

Definitions

The term "acyl" refers to a group represented by the general formula hydrocarbylC(O)—, preferably alkylC(O)—.

The term "acylamino" refers to a moiety that can be represented by the general formula:

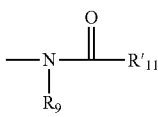

wherein $R_9$ is as defined below, and $R'^{11}$ represents a hydrogen, an alkyl, an alkenyl or —$(CH_2)_m$—$R^8$, where m and $R^8$ are as defined herein.

The term "aliphatic group" refers to a straight-chain, branched-chain, or cyclic aliphatic hydrocarbon group and includes saturated and unsaturated aliphatic groups, such as an alkyl group, an alkenyl group, and an alkynyl group.

The term "alkenyl," as used herein, refers to an aliphatic group containing at least one double bond.

The terms "alkoxyl" or "alkoxy" as used herein refers to an alkyl group, as defined below, having an oxygen radical attached thereto. Representative alkoxyl groups include methoxy, ethoxy, propyloxy, tert-butoxy and the like. An "ether" is two hydrocarbons covalently linked by an oxygen.

The term "alkyl" refers to the radical of saturated aliphatic groups, including straight-chain alkyl groups, branched-chain alkyl groups, cycloalkyl (alicyclic) groups, alkyl-substituted cycloalkyl groups, and cycloalkyl-substituted alkyl groups. In preferred embodiments, a straight chain or branched chain alkyl has 30 or fewer carbon atoms in its backbone (e.g., C1-C30 for straight chains, C3-C30 for branched chains), and more preferably 20 or fewer, and most preferably 10 or fewer. Likewise, preferred cycloalkyls have from 3-10 carbon atoms in their ring structure, and more preferably have 5, 6 or 7 carbons in the ring structure.

The term "alkynyl", as used herein, refers to an aliphatic group containing at least one triple bond.

The term "alkylurea" refers to a group having the structure —NHC(=O)NH-alkyl.

The term "alkylcarbamoyl" refers to a group having the structure —NHCO$_2$-alkyl.

The term "alkylthio" refers to a hydrocarbyl group having a sulfur radical attached thereto. In some embodiments, the "alkylthio" moiety is represented by one of —S-alkyl, —S-alkenyl, or —S-alkynyl. Representative alkylthio groups include methylthio, ethylthio, and the like.

The terms "amine" and "amino" refer to both unsubstituted and substituted amines, e.g., a moiety that can be represented by the general formula:

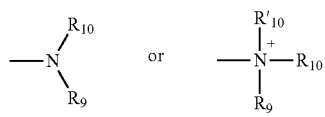

wherein $R_9$, $R_{10}$ and $R'_{10}$ each independently represent a hydrogen, an alkyl, an alkenyl, —(CH$_2$)$_m$—$R_8$, or $R_9$, and $R_{10}$ taken together with the N atom to which they are attached complete a heterocycle having from 4 to 8 atoms in the ring structure; $R_8$ represents an aryl, a cycloalkyl, a cycloalkenyl, an alkoxy, a heterocycle or a polycycle; and m is zero or an integer in the range of 1 to 8.

The term "amido" refers to a moiety that can be represented by the general formula:

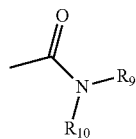

wherein $R_9$, $R_{10}$ are as defined above.

The term "aralkyl", as used herein, refers to an alkyl group substituted with an aryl group (e.g., an aromatic or heteroaromatic group).

The term "aryl" as used herein includes 5-, 6-, and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring can be substituted at one or more ring positions with such substituents as described above, for example, halogen, azide, alkyl, aralkyl, alkenyl, alkynyl, cycloalkyl, polycyclyl, hydroxyl, alkoxyl, amino, nitro, sulfhydryl, imino, amido, phosphate, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls. Each ring can contain, e.g., 5-7 members.

The term "carbocycle or cyclyl," as used herein, refers to an aromatic or non-aromatic ring in which each atom of the ring is carbon.

The term "carbonyl" refers to moieties represented by the general formula:

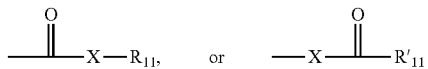

wherein X is a bond or represents an oxygen or a sulfur, and $R_{11}$ represents a hydrogen, an alkyl, an alkenyl, —(CH$_2$)$_m$—$R_8$ or a pharmaceutically acceptable counter-ion, $R'_{11}$ represents a hydrogen, an alkyl, an alkenyl or —(CH$_2$)$_m$—$R_8$, where m and $R_8$ are as defined above. Where X is an oxygen and $R_{11}$ or $R'_{11}$ is not hydrogen, the formula represents an "ester". Where X is an oxygen, and $R_{11}$ is as defined above, the moiety is referred to herein as a carboxyl group, and particularly when $R_{11}$ is a hydrogen, the formula represents a "carboxylic acid". Where X is an oxygen, and $R'_{11}$ is hydrogen, the formula represents a "formate". In general, where the oxygen atom of the above formula is replaced by sulfur, the formula represents a "thiocarbonyl" group. Where X is a sulfur and $R_{11}$ or $R'_{11}$ is not hydrogen, the formula represents a "thioester." Where X is a sulfur and $R_{11}$ is hydrogen, the formula represents a "thiocarboxylic acid." Where X is a sulfur and $R_{11}'$ is hydrogen, the formula represents a "thioformate." On the other hand, where X is a bond, and $R_{11}$ is not hydrogen, the above formula represents a "ketone" group. Where X is a bond, and $R_{11}$ is hydrogen, the above formula represents an "aldehyde" group.

The term "ester", as used herein, refers to a group —C(O)OR$^9$ wherein R$^9$ represents a hydrocarbyl group.

The terms "halo" and "halogen" as used herein means halogen and includes chloro, fluoro, bromo, and iodo.

The terms "hetaralkyl" and "heteroaralkyl", as used herein, refers to an alkyl group substituted with a heteroaryl group.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively). Any ring atom can be substituted (e.g., by one or more substituents).

The terms "heterocyclyl" or "heterocyclic group" refer to 3- to 10-membered ring structures, more preferably 3- to 7-membered rings, whose ring structures include one to four heteroatoms. Heterocycles can also be polycycles, with each group having, e.g., 5-7 ring members. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The term "heterocyclylalkyl", as used herein, refers to an alkyl group substituted with a heterocycle group.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocycle, alkyl, alkenyl, alkynyl, and combinations thereof.

As used herein, the term "nitro" means —NO2; the term "halogen" or "halo" designates —F, —Cl, —Br or —I; the term "sulfhydryl" means —SH; the term "hydroxyl" means —OH; and the term "sulfonyl" means —SO$_2$—.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, 2$^{nd}$ ed.; Wiley: New York, 1991).

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CF$_3$, —CN and the like. Exemplary substituted alkyls are described below. Cycloalkyls can be further substituted with alkyls, alkenyls, alkoxys, alkylthios, aminoalkyls, carbonyl-substituted alkyls, —CF$_3$, —CN, and the like. Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

The term "sulfate" refers to a moiety that can be represented by the general formula:

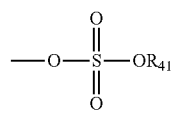

in which R41 is as defined herein.

The term "sulfonamido" refers to a moiety that can be represented by the general formula:

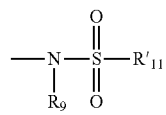

in which R$_9$ and R'$^{11}$ are as defined above.

The term "sulfonate" refers to a moiety that can be represented by the general formula:

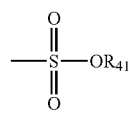

in which R$^{41}$ is an electron pair, hydrogen, alkyl, cycloalkyl, or aryl.

The terms "sulfoxido" or "sulfinyl," as used herein, refers to a moiety that can be represented by the general formula —S(=O)—R44, in which R44 is selected from the group consisting of hydrogen, alkyl, alkenyl, alkynyl, cycloalkyl, heterocyclyl, aralkyl, or aryl.

The term "thioester," as used herein, refers to a group —C(O)SR$^9$ or —SC(O)R$^9$ wherein R$^9$ represents a hydrocarbyl.

As used herein, the definition of each expression, e.g., alkyl, m, n, etc., when it occurs more than once in any structure, is intended to be independent of its definition elsewhere in the same structure.

Exemplary monocyclic rings include furan, thiophene, pyrrole, pyrroline, pyrrolodine, oxazole, thiazole, imidazole, imidazoline, pyrazole, pyrazoline, pyrazolidine, isoxazole, isothiazole, oxadiazole, triazole, thiadiazole, pyran, pyridine, piperidine, dioxane, morpholine, dithiane, thiomorpholine, pyridazine, pyrimidine, pyrazine, piperazine, triazine, and trithiane.

Exemplary bicyclic rings include indolizinyl, indolyl, isoindolyl, indolinyl, benzofuranyl, benzothiophenyl, indazolyl, benzimidazolyl, benthiazolyl, purinyl, quinolizinyl, quinolinyl, isoquinolinyl, cinnolinyl, phthalazinyl, quinazolinyl, quinoxalinyl, naphthyridinyl, pteridinyl, indenyl, naphthalenyl, azulenyl, imidazopyridazionyl, pyrazolopyrimidinedionyl, or pyrrolopyrimidinedionyl moieties.

Exemplary tricyclic rings include carbazole, acridine, phenazine, phenothiazine, phenoxazine, fluorine, and anthracene.

Certain compounds disclosed herein may exist in particular geometric or stereoisomeric forms. The present invention contemplates all such compounds, including cis- and trans-isomers, R- and S-enantiomers, diastereomers, (d)-isomers, (l)-isomers, the racemic mixtures thereof, and other mixtures thereof, as falling within the scope of the invention. For example, if one chiral center is present in a molecule, the invention includes racemic mixtures, enantiomerically enriched mixtures, and substantially enantiomerically pure compounds. The composition can contain, e.g., more than 50%, more than 60%, more than 70%, more than 80%, more than 90%, more than 95%, or more than 99% of a single enantiomer.

The "enantiomeric excess" or "% enantiomeric excess" of a composition can be calculated using the equation shown below. In the example shown below a composition contains 90% of one enantiomer, e.g., the S enantiomer, and 10% of the other enantiomer, i.e., the R enantiomer.

$$ee=(90-10)/100=80\%.$$

Thus, a composition containing 90% of one enantiomer and 10% of the other enantiomer is said to have an enantiomeric excess of 80%.

Methods of preparing substantially isomerically pure compounds are known in the art. If, for instance, a particular enantiomer of a compound disclosed herein is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts may be formed with an appropriate optically active acid or base, followed by resolution of the diastereomers thus formed by fractional crystallization or chromatographic means well known in the art, and subsequent recovery of the pure enantiomers. Alternatively, enantiomerically enriched mixtures and pure enantiomeric compounds can be prepared by using synthetic intermediates that are enantiomerically pure in combination with reactions that either leave the stereochemistry at a chiral center unchanged or result in its complete inversion. Techniques for inverting or leaving unchanged a particular stereocenter, and those for resolving mixtures of stereoisomers are well known in the art, and it is well within the ability of one of skill in the art to choose an appropriate method for a particular situation. See, generally, Furniss et al. (eds.), *Vogel's Encyclopedia of Practical Organic Chemistry* 5*th* Ed., Longman Scientific and Technical Ltd., Essex, 1991, pp. 809-816; and Heller, *Acc. Chem. Res.* 23: 128 (1990).

Contemplated equivalents of the compounds described above include compounds which otherwise correspond thereto, and which have the same general properties thereof (e.g., the ability to inhibit TRPA1 activity), wherein one or more simple variations of substituents are made which do not adversely affect the efficacy of the compound. In general, the compounds disclosed herein may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

The compounds described herein may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds disclosed herein, whether radioactive or not, are intended to be encompassed within the scope of the present invention. For example, deuterated compounds and compounds incorporating $^{13}$C are intended to be encompassed within the scope of the invention.

Certain compounds disclosed herein can exist in unsolvated forms as well as solvated forms, including hydrated forms. In general, the solvated forms are equivalent to unsolvated forms and are encompassed within the scope of the present invention. Certain compounds disclosed herein may exist in multiple crystalline or amorphous forms. In general, all physical forms are equivalent for the uses contemplated by the present invention and are intended to be within the scope of the present invention.

As set out above, certain embodiments of the present compounds may contain a basic functional group, such as amino or alkylamino, and are, thus, capable of forming pharmaceutically acceptable salts with pharmaceutically acceptable acids. The term "pharmaceutically acceptable salts" in this respect, refers to the relatively non-toxic, inorganic and organic acid addition salts of compounds disclosed herein. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", *J. Pharm. Sci.* 66:1-19.)

In other cases, the compounds disclosed herein may contain one or more acidic functional groups and, thus, are capable of forming pharmaceutically acceptable salts with pharmaceutically acceptable bases. The term "pharmaceutically acceptable salts" in these instances refers to the relatively non-toxic, inorganic and organic base addition salts of compounds disclosed herein. These salts can likewise be prepared in situ during the final isolation and purification of the compounds, or by separately reacting the purified compound in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra)

The terms "antagonist" and "inhibitor" are used interchangeably to refer to an agent that decreases or suppresses a biological activity, such as to repress an activity of an ion channel, such as TRPA1. TRPA1 inhibitors include inhibitors having any combination of the structural and/or functional properties disclosed herein.

An "effective amount" of, e.g., a TRPA1 antagonist, with respect to the subject methods of inhibition or treatment, refers to an amount of the antagonist in a preparation which, when applied as part of a desired dosage regimen brings about a desired clinical or functional result. Without being bound by theory, an effective amount of a TRPA1 antagonist for use in the methods of the present invention, includes an amount of a TRPA1 antagonist effective to decrease one or more in vitro or in vivo functions of a TRPA1 channel. Exemplary functions include, but are not limited to, membrane polarization (e.g., an antagonist may promote hyperpolarization of a cell), ion flux, ion concentration in a cell, outward current, and inward current. Compounds that antagonize TRPA1 function include compounds that antagonize an in vitro or in vivo functional activity of TRPA1. When a particular functional activity is only readily observable in an in vitro assay, the ability of a compound to inhibit TRPA1 function in that in vitro assay serves as a reasonable proxy for the activity of that compound. In certain embodiments, an effective amount is an amount sufficient to inhibit a TRPA1-mediated current and/or the amount sufficient to inhibit TRPA1 mediated ion flux.

The term "preventing," when used in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount. Prevention of an infection includes, for example, reducing the number of diagnoses of the infection in a treated population versus an untreated control population, and/or delaying the onset of symptoms of the infection in a treated population versus an untreated control population. Prevention of pain includes, for example, reducing the magnitude of, or alternatively delaying, pain sensations experienced by subjects in a treated population versus an untreated control population.

The term "prodrug" is intended to encompass compounds that, under physiological conditions, are converted into the therapeutically active agents of the present invention. A common method for making a prodrug is to include selected moieties that are hydrolyzed under physiological conditions to reveal the desired molecule. In other embodiments, the prodrug is converted by an enzymatic activity in the host animal.

The terms "TRPA1", "TRPA1 protein", and "TRPA1 channel" are used interchangeably throughout the application. These terms refer to an ion channel (e.g., a polypeptide) comprising the amino acid sequence set forth in SEQ ID NO: 1, SEQ ID NO:3, or SEQ ID NO: 5 of WO 2007/073505, or an equivalent polypeptide, or a functional bioactive fragment thereof. In certain embodiments, the term refers to a polypeptide comprising, consisting of, or consisting essentially of, the amino acid sequence set forth in SEQ ID NO: 1, SEQ ID NO:3, or SEQ ID NO: 5. TRPA1 includes polypeptides that retain a function of TRPA1 and comprise (i) all or a portion of the amino acid sequence set forth in SEQ ID NO: 1, SEQ ID NO:3 or SEQ ID NO: 5; (ii) the amino acid sequence set forth in SEQ ID NO: 1, SEQ ID NO:3 or SEQ ID NO: 5 with 1 to about 2, 3, 5, 7, 10, 15, 20, 30, 50, 75 or more conservative amino acid substitutions; (iii) an amino acid sequence that is at least 70%, 75%, 80%, 90%, 95%, 96%, 97%, 98%, or 99% identical to SEQ ID NO: 1, SEQ ID NO:3 or SEQ ID NO: 5; and (iv) functional fragments thereof. Polypeptides of the invention also include homologs, e.g., orthologs and paralogs, of SEQ ID NO: 1, SEQ ID NO: 3 or SEQ ID NO: 5.

Exemplary compounds are shown below. The $IC_{50}$ values presented in Tables 1-XX were obtained from patch clamp experiments, using human TRPA1, as described in Example 2. An "A" indicates an $IC_{50}$ value less than or equal to 100 nM; a "B" indicates an $IC_{50}$ value of greater than 100 nM and less than 500 nM; a "C" indicates an $IC_{50}$ value of 500 nM to 1000 nM; a "D" indicates an $IC_{50}$ value greater than 1000 nM. Metabolic stability in rat liver microsomes can be determined using techniques described in Kuhnz et al., Drug Metabolism and Disposition (1998) Vol. 26, 1120-27. Oral bioavailability (expressed as % F) can be determined as described in Basic & Clinical Pharmacology, 8th edition, Bertram G. Katzung (editor), Lange Medical Books/McGraw-Hill, 2001.

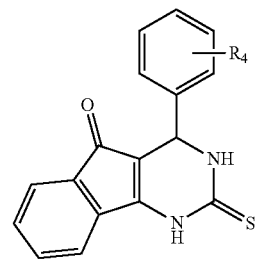

| Compound ID | R4 | Activity |
|---|---|---|
| 1 | 3-OCH2cPr | A |
| 2 | 3-OCH2CH=CH2 | A |
| 3 | 3-OEt | A |
| 4 | 3-OCF2H | A |
| 5 | 3-OMe | A |
| 6 | 3-OCH2CH2OCH3 | A |
| 7 | 2-OH-5-OMe | A |
| 8 | 2-F-5-OMe | A |
| 9 | 2-Br | A |
| 10 | 2-Br-5-OMe | A |
| 11 | 3-Cl | A |
| 12 | 3-CN | A |
| 13 | H | A |
| 14 | 2-F-5-Cl | A |
| 15 | 2-OH | A |
| 16 | 2,6-diCl | B |
| 17 | 3,5-diOMe | B |
| 18 | 2,3-diCl | B |
| 19 | 2-Br-5-OH | B |
| 20 | 2-F | B |
| 21 | 3-NO2 | B |
| 22 | 3-OCH2CH2CH2OCH3 | B |
| 23 | 3-OCH2O-4 | B |
| 24 | 3,4,5-triF | B |
| 25 | 3-OCF3 | B |
| 26 | 3-OH | B |
| 27 | 2,3-naphthalene | B |
| 28 | 2-CF3 | B |
| 29 | 4-OMe | B |
| 30 | 3-OCH2CH2OH | B |
| 31 | 2-Et | B |

-continued

| Compound ID | R4 | Activity |
|---|---|---|
| 32 | 3-F-4-Cl | B |
| 33 | 3-Py* | C |
| 34 | 3,4-diCl | C |
| 35 | 4-CN | C |
| 36 | 2-Cl | C |
| 37 | 4-NO2 | C |
| 38 | 4-Me | D |
| 39 | 3-Br-4-OMe | D |
| 40 | 2-OMe | D |
| 41 | 4-F | D |
| 42 | 2,5-diOMe | D |
| 43 | 2-OEt | D |
| 44 | 3-OMe-4-OH | D |
| 45 | 3,4-diF | D |
| 46 | 4-heptanyl | D |
| 47 | 3-OBu | D |
| 48 | 3-OiPr | D |
| 49 | 4-NMe2 | D |
| 50 | 3-OCH2CH2NMe2 | D |
| 51 | 3-OCH2CH2NH2 | D |
| 52 | 2-OCH2CH=CH2 | |
| 53 | 4-Cl | |

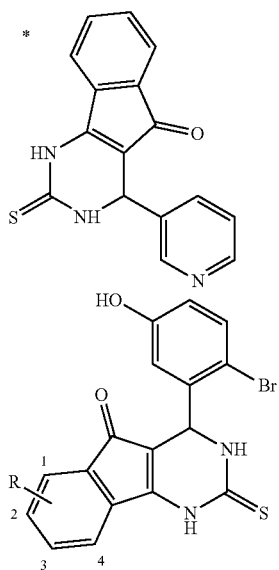

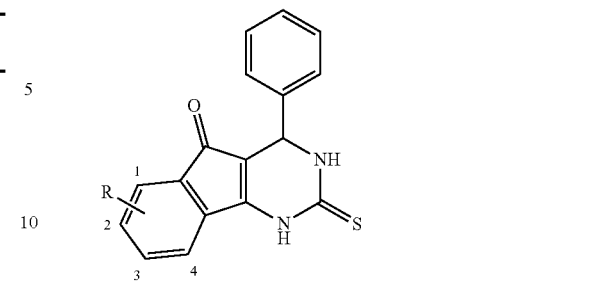

| Compound ID | R | Activity |
|---|---|---|
| 201 | H | A |
| 202 | 1-OH | D |
| 203 | 2-OH | D |
| 204 | 3-OH | D |
| 205 | 3-OMe | B |

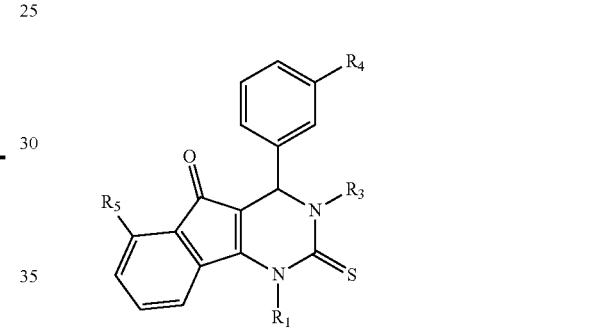

| Compound ID | R1 | R3 | R4 | R5 | Activity |
|---|---|---|---|---|---|
| 301 | H | H | H | H | A |
| 302 | Me | H | H | H | A |
| 303 | H | Me | H | H | D |
| 304 | Me | Me | H | H | D |
| 305 | H | H | OCH2CH=CH2 | H | A |
| 306 | Me | H | OCH2CH=CH2 | H | A |
| 307 | H | H | CN | H | A |
| 308 | Me | H | CN | H | A |
| 309 | H | Me | CN | H | D |
| 310 | H | H | OEt | H | A |
| 311 | Me | H | OEt | H | A |
| 312 | H | H | H | OH | |
| 313 | Me | H | H | OH | D |

| Compound ID | R | Activity |
|---|---|---|
| 101 | 1-Cl | A |
| 102 | H | B |
| 103 | 2-Cl | D |
| 104 | 1-OH | D |
| 105 | 2-OH | D |
| 106 | 3-OH | D |
| 107 | 2-Me | C |

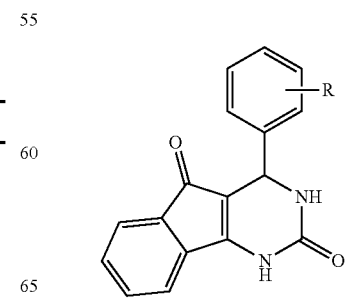

| Compound ID | R | Activity |
|---|---|---|
| 401 | 2-F-3-OCH2CH=CH2 | A |
| 402 | 3-CHFCH2CH=CH2 | A |
| 403 | 3-F-5-OCH2CH=CH2 | A |
| 404 | 2,5-diF-3-OPr | A |
| 405 | 3-OCH2CH=CH2 | A |
| 406 | 3-Cl-5-OCH2CH=CH2 | A |
| 407 | 3-OPr | A |
| 408 | 3-OBu | A |
| 409 | 2-F-3-OEt | A |
| 410 | 2-F-3-OPr | |
| 411 | 2-Cl-3-OCH2CH=CH2 | A |
| 412 | 3-OEt | B |
| 413 | 3-OCH2CF3 | B |
| 414 | 3-OCF2H | B |
| 415 | 2-Cl-5-OCH2CH=CH2 | B |
| 416 | 3-OCH2C≡CH | B |
| 417 | 2-F-5-OCH2CH=CH2 | B |
| 418 | 3-OCH2CH2CH2OMe | B |
| 419 | 2-Cl, 3-OCH2(c-Pr) | B |
| 420 | 2,6-DiF-3-OEt | B |
| 421 | 2-Me-3-OCH2CH=CH2 | B |
| 422 | 3-OCH2cPr | B |
| 423 | 2-Cl-3-OEt | C |
| 424 | 3-OMe | C |
| 425 | 3-OCH2CN | |
| 426 | 2-Cl | C |
| 427 | 3-Bu | C |
| 428 | 2-Cl-3-OMe | D |
| 429 | 2-Cl-5-OMe | D |
| 430 | 3-CN | D |
| 431 | 3-Cl | D |
| 432 | 2-F-5-OMe | D |
| 433 | 2-Br-5-OMe | D |
| 434 | H | D |
| 435 | 2-OH | D |
| 436 | 3-OH | D |
| 437 | 3-OiPr | D |
| 438 | 2,3-diOMe | D |
| 439 | 2-OCH2O-3- | D |
| 440 | 2-OCF2O-3- | D |
| 441 | 2,5-diOMe | D |
| 442 | 4-Cl | D |
| 443 | 3-N(Et)Ac | D |
| 444 | 3-NH2 | D |
| 445 | 3-NMe2 | D |
| 446 | 2,3-diCl | D |
| 447 | 2-F | D |
| 448 | 2-Cl-5-CF3 | D |
| 449 | 2,6-di-Cl | D |
| 450 | 3-OCF2CH3 | D |
| 451 | 3-OCF2CHF2 | D |
| 452 | 3-CF3 | D |
| 453 | 3-CH2OCH3 | D |
| 454 | 2-CF3-3-OCH2CH=CH2 | D |
| 455 | 2-OMe-3-OCH2CH=CH2 | D |
| 456 | 2-OH-3-OCH2CH=CH2 | D |
| 457 | 3-OCH2O-4 | D |
| 458 | 3,5-diOMe | D |
| 459 | 3-OC(O)cPr | D |
| 460 | 3-O-(n-pentyl) | D |
| 461 | 3-OCH2(c-Bu) | D |
| 462 | 3-OCH2CH2OMe | B |

| Compound ID Number | R | Activity |
|---|---|---|
| 501 | pyridin-3-yl | D |
| 502 | thiophen-2-yl | D |
| 503 | 5-ethoxypyridin-3-yl | D |
| 504 | 6-ethoxypyridin-2-yl | C |
| 505 | 2-oxo-2,3-dihydrobenzo[d]oxazol-7-yl | D |
| 506 | 3-ethyl-2-oxo-2,3-dihydrobenzo[d]oxazol-7-yl | D |
| 507 | benzo[c][1,2,5]oxadiazol-4-yl | D |

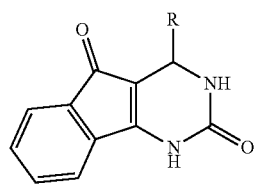

| Compound ID | R4 | R1 | Activity |
|---|---|---|---|
| 601 | 3-OEt | CH2CN | A |
| 602 | 3-OEt | H | B |
| 603 | 3-OEt | Me | A |
| 604 | 3-OEt | Et | A |
| 605 | 3-OEt | CH2CF3 | C |
| 606 | 3-OEt | Bn | A |
| 607 | 3-OEt | CH2(4-F-Ph) | B |
| 608 | 3-OEt | CH2CO2Et | A |
| 609 | 3-OEt | CH2CO2tBu | C |
| 610 | 3-OEt | CH2CO2H | D |
| 611 | 3-OEt | CH2(2-Py) | D |
| 612 | 3-OEt | CH2(3-Py) | B |
| 613 | 3-OEt | CH2(4-Py) | D |
| 614 | 3-OEt | CH2CH=CH2 | B |
| 615 | 3-OPr | CH2CN | A |
| 616 | 2-F-3-OEt | H | A |
| 617 | 2-F-3-OEt | CH2CN | A |
| | 3-OCF2H | H | B |
| 618 | 3-OCF2H | CH2CN | A |
| 619 | 3-OCF2H | Et | B |
| 620 | 3-OCF2H | Bn | A |
| 621 | 3-OMe | H | C |
| 622 | 3-OMe | Me | B |
| 623 | 3-OMe | Et | B |
| 624 | 3-OMe | Pr | D |
| 625 | 3-OMe | Bn | B |
| 626 | 3-OMe | CH2CH2OH | D |
| 627 | 3-OMe | CH2CH2OCH3 | B |
| 628 | 3-OMe | CH2CH2NMe2 | D |
| 629 | 3-OCH2CH=CH2 | Me | A |
| 630 | 3-OCH2CH=CH2 | Et | A |
| 631 | 3-OCH2CH=CH2 | CH2CO2Et | A |
| 632 | 3-OCH2CH=CH2 | Bn | A |
| 633 | 3-OCH2CH=CH2 | CH2(4-F-Ph) | A |
| 634 | 3-OCH2CH=CH2 | CH2(3-Py) | A |
| 635 | 3-OCH2CH=CH2 | CH2(4-Py) | D |
| 636 | 3-OCH2CH=CH2 | CH2(2-Py) | B |
| 637 | 2-Cl-5-OCH2CH=CH2 | H | B |
| 638 | 2-Cl-5-OCH2CH=CH2 | Me | A |
| 639 | 2-Cl-3-OCH2CH=CH2 | Me | A |
| 640 | 2-Cl-3-OCH2CH=CH2 | H | A |
| 641 | 3-OCH2cPr | Me | B |
| 642 | 2-CF3-3-OCH2CH=CH2 | H | D |
| 643 | 2-CF3-3-OCH2CH=CH2 | Me | D |
| 644 | 3-CN | Me | D |
| 645 | 3-OPr | Me | A |
| 646 | 3-OPr | Et | A |
| 647 | 3-OPr | Bn | A |
| 648 | 2,6-DiF-3-OPr | CH2CN | A |
| 649 | 3-OCF2CH=CH2 | Bn | D |

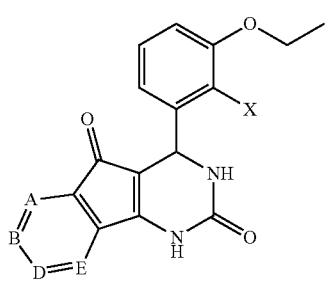

| Compound ID | Substituents | | Activity |
|---|---|---|---|
| 800 | A = CH | | B |
| | B = CH | | |
| | D = CH | | |
| | E = N | | |
| | X = F | | |

| Compound ID | Substituents | | Activity |
|---|---|---|---|
| 801 | A = N | | D |
| | B = CH | | |
| | D = CH | | |
| | E = CH | | |
| | X = F | | |
| 802 | A = CH | | B |
| | B = CH | | |
| | D = CH | | |
| | E = N | | |
| | X = H | | |
| 803 | A = N | | D |
| | B = CH | | |
| | D = CH | | |
| | E = CH | | |
| | X = H | | |
| 804 | A = CH | | C |
| | B = CH | | |
| | D = N | | |
| | E = CH | | |
| | X = H | | |
| 805 | A = CH | | B |
| | B = N | | |
| | D = CH | | |
| | E = CH | | |
| | X = H | | |
| 806 | A = N | | C |
| | B = CH | | |
| | D = CH | | |
| | E = N | | |
| | X = H | | |

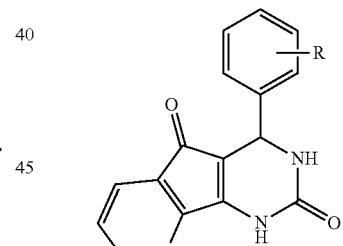

| Compound ID | R | Activity | RLM T1/2 (min) |
|---|---|---|---|
| 901 | 2-F-3-OEt | B | A |
| 902 | 3-OEt | B | A |
| 903 | 3-Bu | B | |
| 904 | 3-OPr | A | |
| 905 | 3-CHFCH2CH=CH2 | A | A |
| 906 | 3-SPr | B | A |
| 907 | 3-CHFPr | A | A |
| 908 | 3-CH(OH)Pr | B | A |
| 909 | 3-C(=O)Pr | B | A |
| 910 | 3-S(=O)Pr | D | |
| 911 | 3-S(=O)2Pr | D | |
| 912 | 2,6-DiF-3-OPr | A | |
| 913 | OCH2CH2CH2OMe | | |

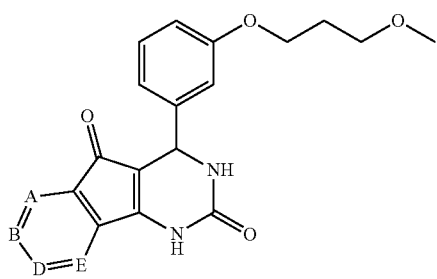
| Compound ID | Substituents | Activity |
|---|---|---|
| 914 | A = CH<br>B = CH<br>D = CH<br>E = CH | B |
| 915 | A = N<br>B = CH<br>D = CH<br>E = CH | D |
| 916 | A = CH<br>B = N<br>D = CH<br>E = CH | D |
| 917 | A = CH<br>B = CH<br>D = N<br>E = CH | D |
| 918 | A = CH<br>B = CH<br>D = CH<br>E = N | D |
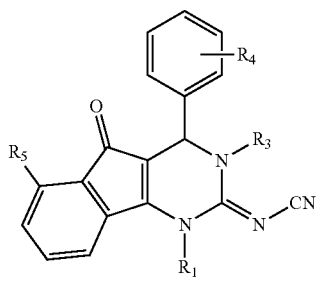
| Compound ID | R4 | R1 | R3 | R5 | Activity |
|---|---|---|---|---|---|
| 950 | 3-OCH2CH=CH2 | H | H | H | D |
| 951 | 3-OCH2cPr | H | H | H | D |
| 952 | 3-OCH2cPr | H | Me | H | D |
| 953 | 3-OCH2cPr | H | Me | Cl | D |
| 954 | 3-OCH2cPr | H | H | Cl | D |
| 955 | 3-CN | H | H | H | D |
| 956 | H | H | H | H | D |
| 957 | 2-Cl-3-OCH2cPr | H | H | H | D |
| 958 | 3-OCH2cBu | H | H | H | D |
| 959 | 3-OiBu | H | H | H | D |
| 960 | 3-OPr | H | H | H | D |
| 961 | 3-OCH2CH=CH2 | Bn | H | H | D |
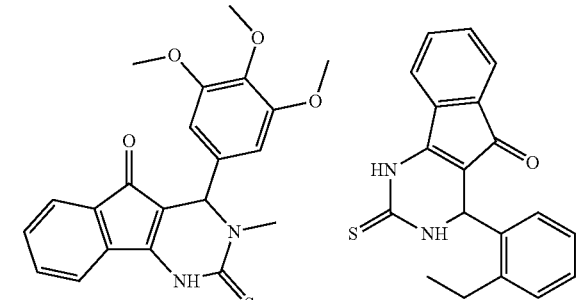
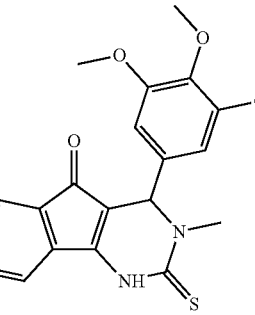
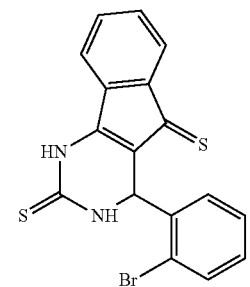
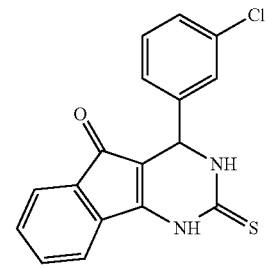
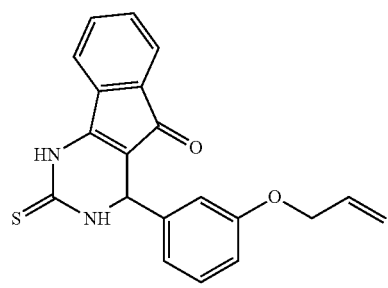

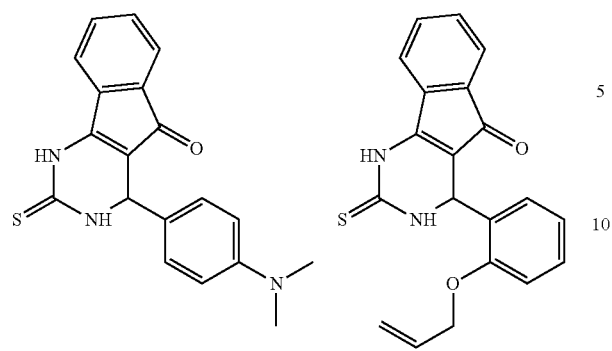
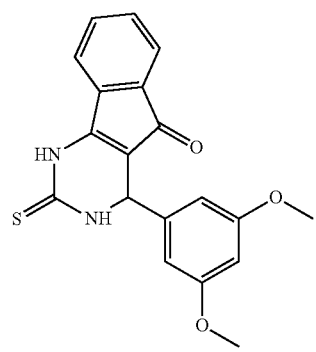

25
-continued
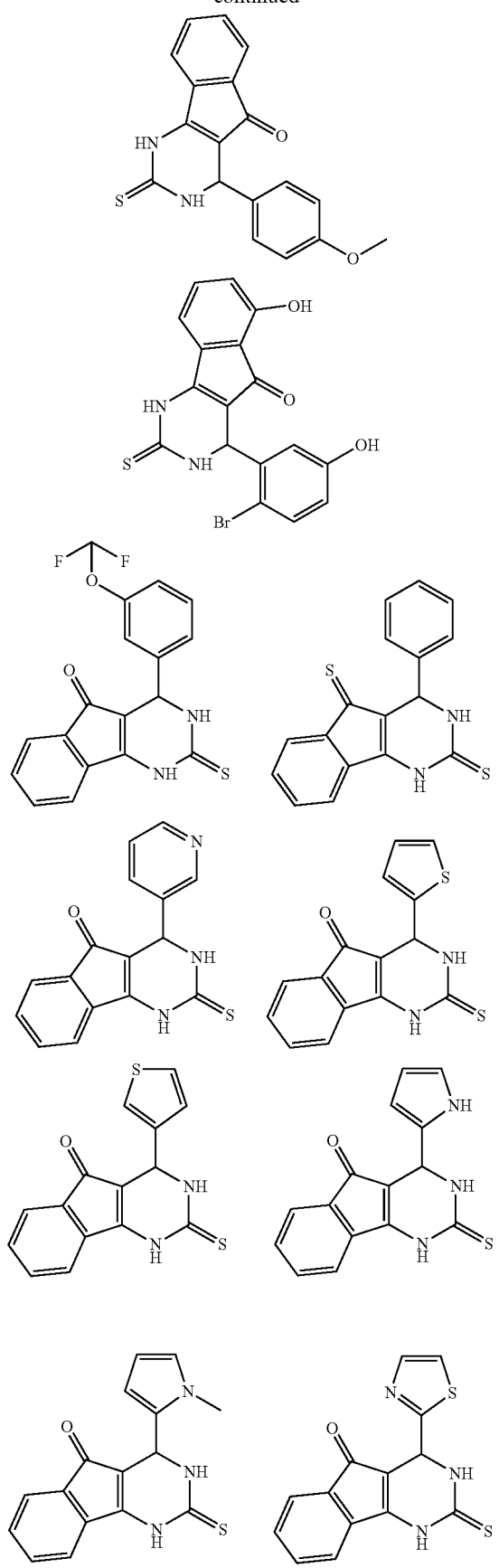
26
-continued
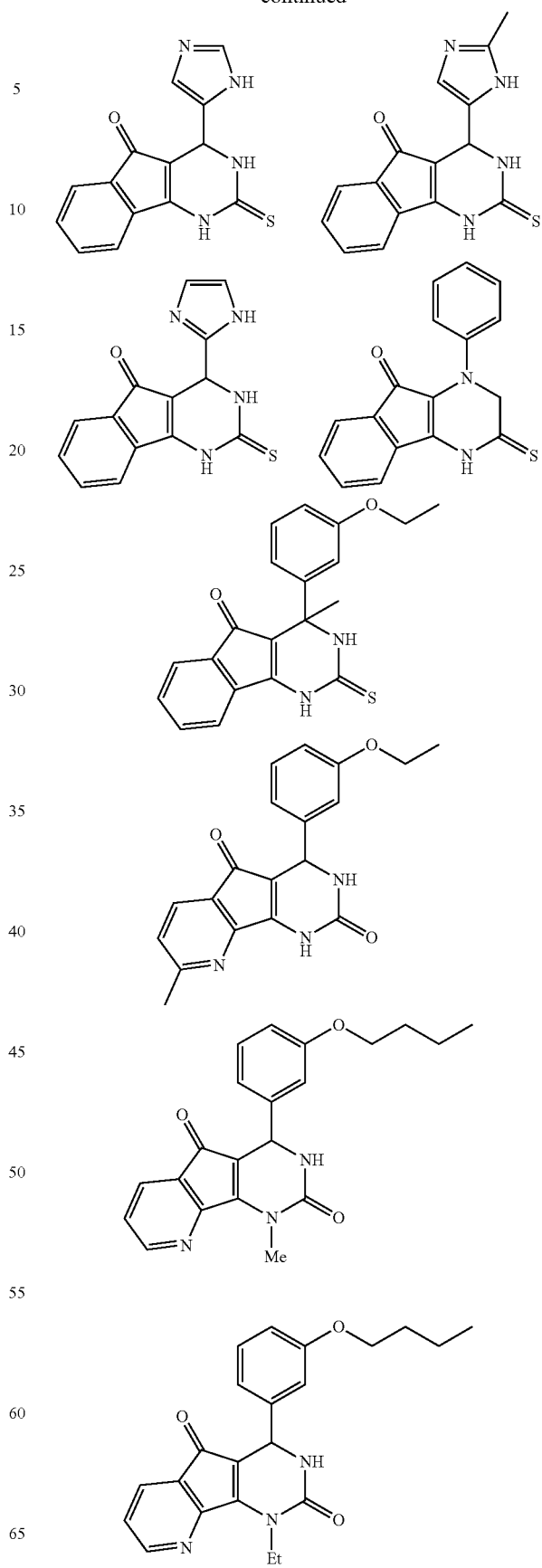

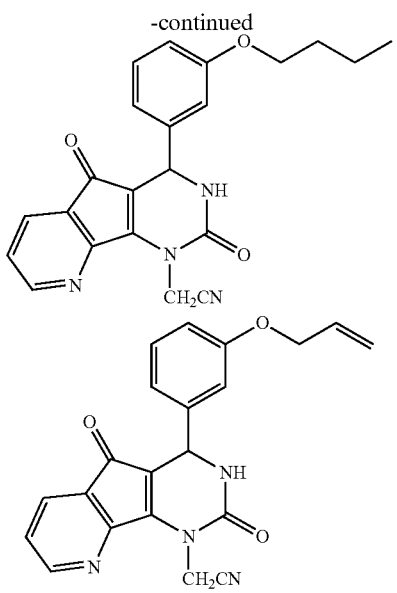

It is believed that the more potent enantiomer is the beta form, which has the R configuration in the compound shown immediately below.

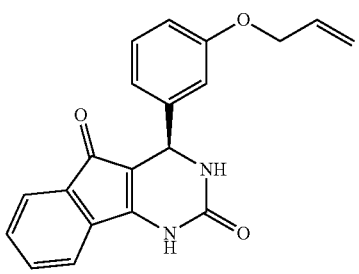 [SMILES: C=CCOc1cccc([C@H]2NC(=O)NC3=C2C(=O)c2ccccc23)c1]

For each compound disclosed herein, it is believed that the enantiomeric form having the stereochemistry illustrated above is more active than the other enantiomer. The enantiomerically pure compounds were prepared by separating the racemic mixture on a chiral column or by converting the racemic mixture into a mixture of diastereomers using an auxiliary chiral moiety, separating the diastereomers on a non-chiral column, then hydrolyzing to remove the auxiliary chiral moiety.

Indications

Cellular homeostasis is a result of the summation of regulatory systems involved in, amongst other things, the regulation of ion flux and membrane potential. Cellular homeostasis is achieved, at least in part, by movement of ions into and out of cells across the plasma membrane and within cells by movement of ions across membranes of intracellular organelles including, for example, the endoplasmic reticulum, sarcoplasmic reticulum, and mitochondria and endocytic organelles including endosomes and lysosomes.

Movement of ions across cellular membranes is carried out by specialized proteins. TRP channels are one large family of non-selective cation channels that function to help regulate ion flux and membrane potential. TRP channels are subdivided into 6 sub-families including the TRPA (ANKTM1) family, and TRPA1 is a member of the TRPA class of TRP channels.

Non-selective cation channels such as TRPA1 modulate the flux of calcium and sodium ions across cellular membranes. Sodium and calcium influx leads to depolarization of the cell. This increases the probability that voltage-gated ion channels will reach the threshold required for activation. As a result, activation of non-selective cation channels can increase electrical excitability and increase the frequency of voltage-dependent events. Voltage-dependent events include, but are not limited to, neuronal action potentials, cardiac action potentials, smooth muscle contraction, cardiac muscle contraction, and skeletal muscle contraction.

Calcium influx caused by the activation of non-selective cation channels such as TRPA1 also alters the intracellular free calcium concentration. Calcium is a ubiquitous second messenger molecule within the cell, so alterations in intracellular calcium levels have profound effects on signal transduction and gene expression. As a result, activation of non-selective cation channels such as TRPA1 can lead to changes in gene expression and cellular phenotype. Gene expression events include, but are not limited to, production of mRNAs encoding cell surface receptors, ion channels, and kinases. These changes in gene expression can lead to hyperexcitability in that cell.

TRPA1 proteins are broad receptors for noxious chemicals, both endogenous and exogenous. They respond to any of a variety of stimuli that can induce cysteine modificaction (Hinman et al., 2006; MacPherson et al. 2007). In addition TRPA1 can function as a receptor operated channel. It expressed in sensory neurons (see, e.g., Jordt et al. (2004) Nature 427:260-265) including those with cell bodies residing in the dorsal root ganglion, trigeminal ganglion, and nodose ganglia (see Jordt et al. (2004) Nature 427:260-265, Nagata et al. (2005) J. Neurosci 25(16) 4052-61). In addition, low levels of TRPA1 message can be found in some types of fibroblasts (see Jaquemar et al. (1999) JBC 274(11): 7325-33). TRPA1 has also been reported to be expressed in the bladder. Stimulation of a number of extracellular receptors, including, but not limited to, G-protein coupled receptors or receptor tyrosine kinases are sufficient to activate TRPA1.

Modulating the function of TRPA1 proteins provides a means of modulating calcium homeostasis, sodium homeostasis, membrane polarization, and/or intracellular calcium levels, and compounds that can modulate TRPA1 function are useful in many aspects, including, but not limited to, maintaining calcium homeostasis, modulating intracellular calcium levels, modulating membrane polarization, and treating or preventing diseases, disorders, or conditions associated with calcium and/or sodium homeostasis or dyshomeostasis.

Thus, TRPA1 antagonists can be used as part of a prophylaxis or treatment for a variety of disorders and conditions, described in more detail below. In other embodiments, the invention provides methods and compositions for inhibiting a function of a TRPA1 channel in vitro or in vivo. The compounds described herein can be used in the treatment of any of the foregoing or following diseases or conditions, including in the treatment of pain associated with any of the foregoing or following diseases or conditions.

Injuries from Chemical Warfare Agents

The compounds disclosed herein can be useful for the treatment and prevention of injuries resulting from the exposure to chemical warfare agents. Such injuries include any physical injuries, such as injuries to the skin (e.g., burn, inflammation, burn, and rash), eyes, respiratory tract, musculo-skeletal system, circulatory system, gastrointestinal tract, central nervous system, peripheral nervous system, heart, liver, lungs, and kidneys. The compound is administered to a subject before, during, or following such exposure and is therefore administered within 24 hours, 18 hours, 6 hours, 4 hours, 3 hours, 2 hours, 1 hour, 30 minutes, 20 minutes, 10 minutes, 5 minutes, one minute, or thirty seconds of such exposure. A subject may be exposed to a chemical warfare agent by inhalation or touching. As a result of such administration, the symptoms or injuries resulting from the exposure of chemical warfare agents are reduced, prevented, or both. Exemplary symptoms or injuries resulting from the exposure to chemical warfare agents include inflammation, burn, itch, pain, rash, blisters, sweating, muscle twitching, nausea, vomiting, diarrhea, weakness, loss of conciousness, convulsions, muscular twitching, paralysis, secretions (from the mouth, nose, or lung for example), difficulty breathing, blurred vision, eye pain, lacrimation, red eyes, shortness of breath, coughing, phlegm production and narrowing of the airways, headaches, tremors, dizziness, numbness or tingling, anxiety, insomnia, depression, emotional instability, and even death. These chemical warfare agents include all those classified as schedule 1, 2, and 3 agents under the Chemical Weapons Convention of 1993 and may be in liquid form, gas form, solid form, or combinations thereof. Exemplary agents are described in further detail below and include, for example, nerve agents, blood agents, blister agents, pulmonary agents, incapacitating agents, and toxins.

Nerve agent poisoning typically leads to contraction of pupils, profuse salivation, convulsions, involuntary urination and defecation, and eventual death by asphyxiation as control is lost over respiratory muscles. These symptoms are reduced or prevented by the administration of the TRPA1 antagonists. Exemplary agents include G agents such as tabun (GA), sarin (GB), soman (GD), cyclosarin (GF), and GV; V agents such as VE, VG, VM, VX, and Novichok agents. For example, in addition to wearing a full body suit and a gas mask, subjects who are likely to be exposed to such agents are administered a TRPA1 antagonist.

A blood agent (or cyanogen agent) is a compound containing a cyanide group that prevents the body from utilizing oxygen. These agents exert their toxic effect at the cellular level by directly interrupting cellular respiration. Exemplary agents include cyanogen chloride, hydrogen cyanide, and hydrogen sulfide.

Blister agents or vesicants typically cause severe skin, eye and mucosal pain and irritation. These agents also have the ability to cause large, painful water blisters. Blister agents include, for example, lewisites, nitrogen mustard, sulfur mustard, ethyldichloroarsine (a lewisite analog; ED), methyldichloroarsine (MD), phenyldichloroarsine (PD), and phosgene oxime (CX). Lewisites include, for example, 2-Chlorovinyldichloroarsine (Lewisite 1), Bis(2-chlorovinyl)chloroarsine (Lewisite 2), and Tris(2-chlorovinyl)arsine (Lewisite 3). Exemplary nitrogen mustards are bis(2-chloroethyl)ethylamine (HN1), bis(2-chloroethyl)methylamine (HN2), and tris(2-chloroethyl)amine (HN3). Sulfur mustards include, for example, 1,2-Bis(2-chloroethylthio) ethane (Sesquimustard; Q), 1,3-Bis(2-chloroethylthio)-n-propane, 1,4-Bis(2-chloroethylthio)-n-butane, 1,5-Bis(2-chloroethylthio)-n-pentane, 2-Chloroethylchloromethylsulfide, bis(2-chloroethyl) sulfide (Mustard gas; HD), bis(2-chloroethylthio) methane, bis(2-chloroethylthiomethyl) ether, and bis(2-chloroethylthioethyl)ether (O Mustard).

A pulmonary agent (or choking agent) is a chemical weapon agent designed to impede a subject's ability to breathe, resulting in suffocation. Exemplary agents include adamsite (DM), acrolein, bis(chloromethyl)ether (BCME), chlorine (C12), chloropicrin (PS), diphosgene (DP), methyl chlorosulfonate, phosgene (CG), and stannic chloride. Incapacitating agents or riot-control agents typically produce temporary physiological or mental effects, or both, such that individuals who are exposed to them are incapable of concerted effort. Upon their exposure, lachrymatory agents (or lachrymators) for example, irritate the eyes to cause tearing, pain, and even temporary blindness. The most common lachrymatory agents are tear gas and pepper spray and include, for example, a-Chlorotoluene, benzyl bromide, bromoacetone (BA), bromobenzylcyanide (CA) bromomethyl ethyl ketone, capsaicin (OC), chloracetophenone (Tear gas; CN), chloromethyl chloroformate, dibenzoxazepine (CR), ethyl iodoacetate, ortho-chlorobenzylidene malononitrile (Super tear gas; CS), trichloromethyl chloroformate, and xylyl bromide. Other incapacitating agents include, for example, 3-Quinuclidinyl benzilate (psychedelic; BZ), hydrocyanic acid (paralytic), diphenylchloroarsine (sternutatory; DA), diphenylcyanoarsine (DC), and KOLOKOL-1 (tranquilizer).

Exemplary toxins include abrin, ricin, and saxitoxin.

In addition to TRPA1, other TRP channels have been implicated in pain reception and/or sensation. For example, certain TRPM channels including TRPM8 have been implicated in the reception and/or sensation of pain. Accordingly, in certain embodiments, the methods of the present invention include treating pain by administering (i) a combination of a selective TRPA1 antagonist and a selective TRPM8 antagonist; (ii) a combination of a selective TRPA1 antagonist, a selective TRPM8 antagonist, and one or more of a selective TRPV1 and/or TRPV3 antagonist; (iii) a cross-TRP inhibitor that antagonizes a function of TRPA1 and TRPM8; or (iv) a pan inhibitor that antagonizes a function of TRPA1, TRPM8, and one or more of TRPV1 and TRPV3.

In certain embodiments, a compound of the invention is conjointly administered with one or more additional compounds that antagonize the function of a different channel. By way of example, a compound of the invention may be conjointly administered with one or more compounds that antagonize TRPV1, TRPM8, and/or TRPV3. The compound(s) that antagonize TRPV1, TPRM8, or TRPV3 may be selective for TRPV1, TRPM8 or TRPV3 (e.g., inhibit TRPV1 or TRPV3 10, 100, or 1000 fold more strongly than TRPA1). Alternatively, the compound(s) that antagonize TRPV1 or TRPV3 may cross react with other TRP channels.

Pharmaceutical Compositions

While it is possible for a compound disclosed herein to be administered alone, it is preferable to administer the compound as a pharmaceutical formulation, where the compound is combined with one or more pharmaceutically acceptable excipients or carriers. The compounds disclosed herein may be formulated for administration in any convenient way for use in human or veterinary medicine. In certain embodiments, the compound included in the pharmaceutical preparation may be active itself, or may be a prodrug, e.g., capable of being converted to an active compound in a physiological setting.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Examples of pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; (21) cyclodextrins such as anionically charged sulfobutyl ether β-cyclodextrins or hydroxypropyl-beta-cyclodextrins; and (22) other non-toxic compatible substances employed in pharmaceutical formulations.

Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Solid dosage forms (e.g., capsules, tablets, pills, dragees, powders, granules and the like) can include one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents.

Liquid dosage forms can include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

The tablets, and other solid dosage forms of the pharmaceutical compositions disclosed herein, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The formulations disclosed herein can be delivered via a device. Exemplary devices include, but are not limited to, a catheter, wire, stent, or other intraluminal device. Further exemplary delivery devices also include a patch, bandage, mouthguard, or dental apparatus. Transdermal patches have the added advantage of providing controlled delivery of a compound disclosed herein to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, drops, solutions and the like, are also contemplated as being within the scope of this invention.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

When the compounds disclosed herein are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The formulations can be administered topically, orally, transdermally, rectally, vaginally, parentally, intranasally, intrapulmonary, intraocularly, intravenously, intramuscularly, intraarterially, intrathecally, intracapsularly, intraorbitally, intracardiacly, intradermally, intraperitoneally, transtracheally, subcutaneously, subcuticularly, intraarticularly, subcapsularly, subarachnoidly, intraspinally, intrasternally or by inhalation.

One specific embodiment is an antitussive composition for peroral administration comprising an agent that inhibits both a TRPA1-mediated current with an $IC_{50}$ of 1 micromolar or less, and an orally-acceptable pharmaceutical carrier in the form of an aqueous-based liquid, or solid dissolvable in the mouth, selected from the group consisting of syrup, elixer, suspension, spray, lozenge, chewable lozenge, powder, and chewable tablet. Such antitussive compositions can include one or more additional agents for treating cough, allergy or asthma symptom selected from the group consisting of: antihistamines, 5-lipoxygenase inhibitors, leukotriene inhibitors, H3 inhibitors, β-adrenergic receptor agonists, xanthine derivatives, a-adrenergic receptor agonists, mast cell stabilizers, expectorants, NK1, NK2 and NK3 tachykinin receptor antagonists, and $GABA_B$ agonists.

Still another embodiment is a metered dose aerosol dispenser containing an aerosol pharmaceutical composition for pulmonary or nasal delivery comprising an agent that inhibits a TRPA1-mediated current with an $IC_{50}$ of 1 micromolar or less. For instance, it can be a metered dose inhaler, a dry powder inhaler or an air-jet nebulizer.

Dosages

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound disclosed herein employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound that is the lowest dose effective to produce a therapeutic effect. Such an effective dose will generally depend upon the factors described above. Generally, intravenous, intracerebroventricular and subcutaneous doses of the compounds of this invention for a patient will range from about 0.0001 to about 100 mg per kilogram of body weight per day. For example, the dose can be 1-50, 1-25, or 5-10 mg/kg.

If desired, the effective daily dose of the active compound may be administered as two, three, four, five, six or more sub-doses administered separately at appropriate intervals throughout the day, optionally, in unit dosage forms.

Disease and Injury Models

Compounds that antagonize TRPA1 function may be useful in the prophylaxis and treatment of any of the foregoing injuries, diseases, disorders, or conditions. In addition to in vitro assays of the activity of these compounds, their efficacy can be readily tested in one or more animal models. There are numerous animal models for studying pain. The various models use various agents or procedures to simulate pain resulting from injuries, diseases, or other conditions. Blackburn-Munro (2004) Trends in Pharmacological Sciences 25: 299-305 (see, for example, Tables 1, 3, or 4). Behavioral characteristics of challenged animals can then be observed. Compounds or procedures that may reduce pain in the animals can be readily tested by observing behavioral characteristics of challenged animals in the presence versus the absence of the test compound(s) or procedure.

Exemplary behavioral tests used to study chronic pain include tests of spontaneous pain, allodynia, and hyperalgesia. Id. To assess spontaneous pain, posture, gait, nocifensive signs (e.g., paw licking, excessive grooming, excessive exploratory behavior, guarding of the injured body part, and self-mutilation) can be observed. To measure evoked pain, behavioral responses can be examined following exposure to heat (e.g., thermal injury model).

Exemplary animal models of pain include, but are not limited to, the Chung model, the carageenan induced hyperalgesia model, the Freund's complete adjuvant induced hyperalgesia model, the thermal injury model, the formalin model and the Bennett Model. The Chung model of neuropathic pain (without inflammation) involves ligating one or more spinal nerves. Chung et al. (2004) Methods Mol Med 99: 35-45; Kim and Chung (1992) Pain 50: 355-363. Ligation of the spinal nerves results in a variety of behavioral changes in the animals including heat hyperalgesia, cold allodynia, and ongoing pain. Compounds that antagonize TRPA1 can be administered to ligated animals to assess whether they diminish these ligation-induced behavioral changes in comparison to that observed in the absence of compound.

Carageenan induced hyperalgesia and Freund's complete adjuvant (FCA) induced hyperalgesia are models of inflammatory pain. Walker et al. (2003) Journal of Pharmacol Exp Ther 304: 56-62; McGaraughty et al. (2003) Br J Pharmacol 140: 1381-1388; Honore et al. (2005) J Pharmacol Exp Ther. Compounds that antagonize TRPA1 can be administered to carrageenan or FCA challenged animals to assess whether they diminish thermal hyperalgesia in comparison to that observed in the absence of compound. In addition, the ability of compounds that antagonize TRPA1 function to diminish cold and/or mechanical hypersensitivity can also be assessed in these models. Typically, the carrageenan induced hyperalgesia model is believed to mimic acute inflammatory pain and the CFA model is believed to mimic chronic pain and chronic inflammatory pain.

Exemplary models of inflammatory pain include the rat model of intraplantar bradykinin injection. Briefly, the baseline thermal sensitivity of the animals is assessed on a Hargreave's apparatus. TRPA1 blockers are then administered systemically. Bradykinin is subsequently injected into the paw and a hyperalgesia is allowed to develop. Thermal escape latency is then measured at multiple time points over the next few hours (Chuang et al., 2001; Vale et al., 2004).

Inflammation is often an important contributing factor to pain. As such, it is useful to identify compounds that act as anti-inflammatories. Many compounds that reduce neural activity also prevent neurogenic inflammation. To measure inflammation directly, the volume of a rat paw can be assessed using a plethysmometer. After baseline measurement is taken, carrageenan can be injected into the paw and the volume can be monitored over the course of hours in animals that have been treated with vehicle or drug. Drugs that reduce the paw swelling are considered to be anti-inflammatory.

Migraines are associated with significant pain and inability to complete normal tasks. Several models of migraine exist including the rat neurogenic inflammation model, (see Buzzi et al (1990) Br J Pharmacol; 99:202-206), and the Burstein Model (see Strassman et al., (1996) Nature 384: 560-564).

The Bennett model uses prolonged ischemia of the paw to minor chronic pain. Xanthos et al. (2004) J Pain 5: S1. This provides an animal model for chronic pain including postoperative pain, complex regional pain syndrome, and reflex sympathetic dystrophy. Prolonged ischemia induces behavioral changes in the animals including hyperalgesia to mechanical stimuli, sensitivity to cold, pain behaviors (e.g., paw shaking, licking, and/or favoring), and hyperpathia. Compounds that antagonize TRPA1 can be administered to challenged animals to assess whether they diminish any or all of these behaviors in comparison to that observed in the absence of compound. Similar experiments can be conducted in a thermal injury or UV-burn model which can be used to mimic post-operative pain.

Additional models of neuropathic pain include central pain models based on spinal cord injury. Chronic pain is generated by inducing a spinal cord injury, for example, by dropping a weight on a surgically exposed area of spinal cord (e.g., weight-drop model). Spinal cord injury can additionally be induced by crushing or compressing the spinal cord, by delivering neurotoxin, using photochemicals, or by hemisecting the spinal cord. Wang and Wang (2003).

Additional models of neuropathic pain include peripheral nerve injury models. Exemplary models include, but are not limited to, the neuroma model, the Bennett model, the Seltzer model, the Chung model (ligation at either L5 or L5/L6), the sciatic cryoneurolysis model, the inferior caudal trunk resection model, and the sciatic inflammatory neuritis model. Id.

Exemplary models of neuropathic pain associated with particular diseases are also available. Diabetes and shingles are two diseases often accompanied by neuropathic pain. Even following an acute shingles episodes, some patients continue to suffer from postherpetic neuralgia and experience persistent pain lasting years. Neuropathic pain caused by shingles and/or postherpetic neuralgia can be studied in the postherpetic neuralgia model (PHN). Diabetic neuropathy can be studied in diabetic mouse models, as well as chemically induced models of diabetic neuropathy. Wang and Wang (2003).

As outlined above, cancer pain may have any of a number of causes, and numerous animal models exist to examine cancer pain related to, for example, chemotherapeutics or tumor infiltration. Exemplary models of toxin-related cancer pain include the vincristine-induced peripheral neuropathy model, the taxol-induced peripheral neuropathy model, and the cisplatin-induced peripheral neuropathy model. Wang and Wang (2003). An exemplary model of cancer pain caused by tumor infiltration is the cancer invasion pain model (CIP). Id.

Primary and metastatic bone cancers are associated with tremendous pain. Several models of bone cancer pain exist including the mouse femur bone cancer pain model (FBC), the mouse calcaneus bone cancer pain model (CBC), and the rat tibia bone cancer model (TBC). Id.

An additional model of pain is the formalin model. Like the carrageenan and CFA models, the formalin model involves injection of an irritant intradermally or intraperitoneally into an animal. Injection of formalin, a 37 percent solution of formaldehyde, is the most commonly used agent for intradermal paw injection (the formalin test). Injection of a 0.5 to 15 percent solution of formalin (usually about 3.5%) into the dorsal or plantar surface of the fore- or hindpaw produces a biphasic painful response of increasing and decreasing intensity for about 60 minutes after the injection. Typical responses include the paw being lifted, licked, nibbled, or shaken. These responses are considered nociceptive. The initial phase of the response (also known as the Early Phase), which lasts 3 to 5 minutes, is probably due to direct chemical stimulation of nociceptors. This is followed by 10 to 15 minutes during which animals display little behavior suggestive of nociception. The second phase of this response (also known as the Late Phase) starts about 15 to 20 minutes after the formalin injection and lasts 20 to 40 minutes, initially rising with both number and frequency of nociceptive behaviors, reaching a peak, then falling off. The intensities of these nociceptive behaviors are dependent on the concentration of formalin used. The second phase involves a period of sensitization during which inflammatory phenomena occur. The two phases of responsiveness to formalin injection makes the formalin model an appropriate model for studying mociceptive and acute inflammatory pain. It may also model, in some respects, neuropathic pain.

In addition to any of the foregoing models of chronic pain, compounds that antagonize TRPA1 function can be tested in one or more models of acute pain. Valenzano et al. (2005) Neuropharmacology 48: 658-672. Regardless of whether compounds are tested in models of chronic pain, acute pain, or both, these studies are typically (though not exclusively) conducted, for example, in mice, rats, or guinea pigs. Additionally, compounds can be tested in various cell lines that provide in vitro assays of pain. Wang and Wang (2003).

Many individuals seeking treatment for pain suffer from visceral pain Animal models of visceral pain include the rat model of inflammatory uterine pain (Wesselmann et al., (1997) Pain 73:309-317), injection of mustard oil into the gastrointestinal tract to mimic irritable bowel syndrome (Kimball et al., (2005) Am J Physiol Gastrointest Liver Physiol, 288(6):G1266-73), injection of mustard oil into the bladder to mimic overactive bladder or bladder cystitis (Riazimand (2004), BJU 94: 158-163). The effectiveness of a TRPA1 compound can be assessed by a decrease in writhing, gastrointestinal inflammation or bladder excitability.

For testing the efficacy of TRPA1 antagonists for the treatment of cough, experiments using the conscious guinea pig model of cough can be readily conducted. Tanaka and Maruyama (2003) Journal Pharmacol Sci 93: 465-470; McLeod et al. (2001) Br J Pharmacol 132: 1175-1178. Briefly, guinea pigs serve as a useful animal model for cough because, unlike other rodents such as mice and rats, guinea pigs actually cough. Furthermore, guinea pig coughing appears to mimic human coughing in terms of the posture, behavior, and appearance of the coughing animal.

To induce cough, conscious guinea pigs are exposed to an inducing agent such as citric acid or capsaicin. The response of the animal is measured by counting the number of coughs. The effectiveness of a cough suppressing agent, for example a compound that inhibits TRPA1, can be measured by administering the agent and assessing the ability of the agent to decrease the number of coughs elicited by exposure to citric acid, capsaicin, or other similar cough-inducing agent. In this way, TRPA1 inhibitors for use in the treatment of cough can be readily evaluated and identified.

Additional models of cough include the unconscious guinea pig model. Rouget et al. (2004) Br J Pharmacol 141: 1077-1083. Either of the foregoing models can be adapted for use with other animals capable of coughing. Exemplary additional animals capable of coughing include cats and dogs.

Numerous rodent models of incontinence exist. These include models of incontinence induced by nerve damage, urethral impingement and inflammation. Models of urethral impingement include the rat bladder outflow obstruction model. (Pandita, R K, and Andersson K E. Effects of intravesical administration of the K+ channel opener, Z.D6169, in conscious rats with and without bladder outflow obstruction. J Urol 162: 943-948, 1999). Inflammatory models include injection of mustard oil into the bladder.

To test the effectiveness of a TRPA1 inhibitor compound in treating incontinence, varying concentrations of compound (e.g., low, medium, and high concentration) can be administered to rats following surgical partial bladder outlet obstruction (BOO). Efficacy of the varying doses of TRPA1 inhibitory compound can be compared to controls administered excipients alone (sham control). Efficacy can further be compared to rats administered a positive control, such as atropine. Atropine is expected to decrease bladder over-activity following partial bladder outlet obstruction in the BOO model. Note that when testing compounds in the BOO model, compounds can be administered directly to the bladder or urethra (e.g., by catheter) or compounds can be administered systemically (e.g., orally, intraveneously, intraperitoneally, etc).

Several rat models of pancreatitic pain have recently been described (Lu, 2003, Anesthesiology 98(3): 734-740; Winston et al., 2003, Journal of Pain 4(6): 329-337). Lu et al. induced pancreatitis by systemic delivery of dibutylin dichloride in rats. Rats showed an increase in withdrawal events after von Frey filament stimulation of the abdomen and decreased withdrawal latency after thermal stimulation during a period of 7 days. The pain state induced in these animals was also characterized by increased levels of substance P in spinal cords (Lu, et al., 2003). To test the efficacy of a TRPA1 inhibitor in this model, a TRPA1 inhibitor can be administered following or concurrently with delivery of dibutylin dichloride. Control animals can be administered a carrier or a known pain reliever. Indicia of pain can be measured. Efficacy of a TRPA1 inhibitor can be evaluated by comparing the indicia of pain observed in animals receiving a TRPA1 inhibitor to that of animals that did not receive a TRPA1 inhibitor. Additionally, efficacy of a TRPA1 inhibitor can be compared to that of known pain medications.

The efficacy of von Frey filament testing as a means to measure nociceptive behavior was also shown by inducing pancreatitis by systemic L-arginine administration (Winston et al, 2003). The efficacy of a TRPA1 inhibitor can similarly be tested following pancreatitis induced by systemic L-arginine administration.

Lu et al. also described direct behavioral assays for pancreatic pain using acute noxious stimulation of the pancreas via an indwelling ductal canula in awake and freely moving rats. These assays included cage crossing, rearing, and hind limb extension in response to intrapancreatic bradykinin infusion. Intrathecal administration of either D-APV (NMDA receptor antagonist) or morphine alone partially reduced visceral pain behaviors in this model. Combinations of both reduced pain behaviors to baseline. The efficacy of a TRPA1 inhibitor can similarly be tested in this system.

Any of the foregoing animal models may be used to evaluate the efficacy of a TRPA1 inhibitor in treating pain associated with pancreatitis. The efficacy can be compared to a no treatment or placebo control. Additionally or alternatively, efficacy can be evaluated in comparison to one or more known pain relieving medicaments.

The following examples are meant to be illustrative and are not meant to be limiting in any way.

EXAMPLES

Example 1

Synthesis of Exemplary Compounds

The compounds disclosed herein can be prepared using the scheme outlined below.

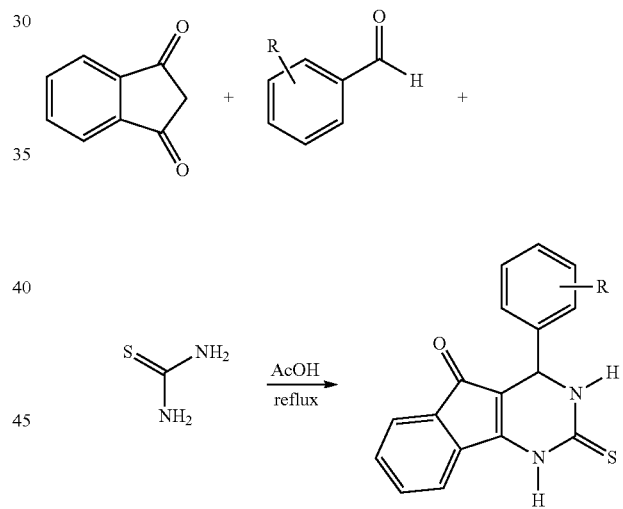

Example 2

Synthesis of Additional Exemplary Compounds

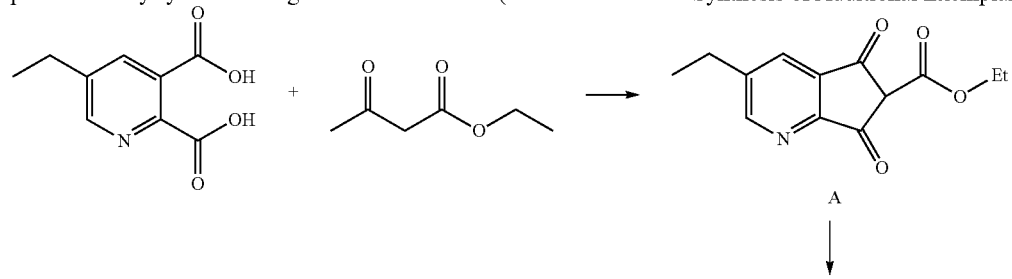

A

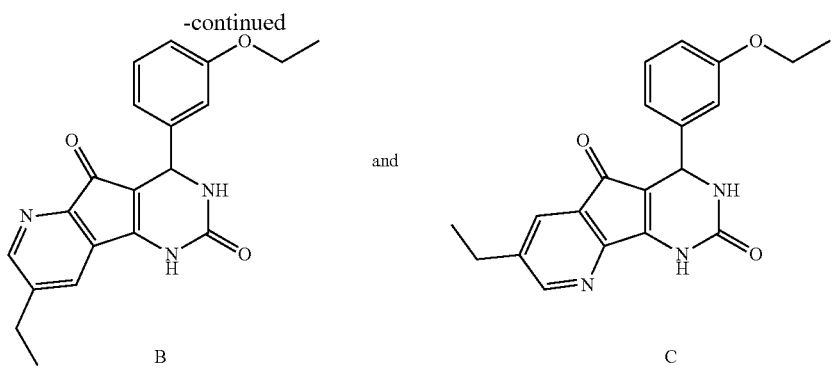

Ethyl 3-ethyl-5,7-dioxo-6,7-dihydro-5H-cyclopenta[b]pyridine-6-carboxylate (Compound A):

The mixture of 5-ethylpyridine-2,3-dicarboxylic acid (1.620 g, 8.3 mmol) in anhydrous $Ac_2O$ (4.7 mL) was mixed and cooled to 0° C. To this mixture at 0° C. was slowly added was slowly added ethyl 3-oxobutanoate (1.05 mL, 8.3 mmol) and anhydrous $Et_3N$ (2.3 mL, 16.6 mol) and then the reaction was allowed to stir at room temperature for 3 days. The reaction was diluted with HCl aqueous solution (90 mL, 0.27 M). The aqueous phase was washed with ethyl acetate twice. Golden needle crystal was crystallized out from aqueous phase to give the target compound (949 mg, 46%).

Compound B and C:

Ethyl 3-ethyl-5,7-dioxo-6,7-dihydro-5H-cyclopenta[b]pyridine-6-carboxylate (600 mg, 2.4 mmol), 3-ethoxybenzaldehyde (364 mg, 2.4 mmol) and urea (288 mg, 4.8 mmol) was added to acetic acid (2.5 mL) and the reaction was heated at 90° C. for 4 hours. The reaction was concentrated in high vacuo. The residue was purified by column chromatography (MeOH: DCM=1:100 to 1:25) to give the target compound B (20 mg) and compound C (14.4 mg) as yellow solids. The structures were determined by $^1H$-$^{13}C$ HMBC NMR

Example 2

Patch Clamp Experiments

Patch clamp experiments permit the detection of currents through the TRPA1 channel in the cell line described above. The whole-cell configuration of the patch clamp technique was used to test the compounds described herein. In normal whole-cell patch clamp recordings, a glass electrode is brought into contact with a single cell and a high-resistance (gigaohm) seal is established with the cell membrane. The membrane is then ruptured to achieve the whole-cell configuration, permitting control of the voltage of the cell membrane and measurement of currents flowing across the membrane using the amplifier attached to the electrode and resulting in the replacement of cytoplasm with the pipette solution.

TRPA1 cells were induced 20-48 hours, removed from growth plates, and replated at low density (to attain good single-cell physical separation) on glass coverslips for measurement. In some cases, cells were grown in low density overnight on glass coverslips. Potential blockers were tested for ability to block current in the continued presence of AITC.

Example 3

Testing of TRPA1 Antagonists in a Thermal Injury Model of Pain

The thermal injury model can be used to evaluate the effectiveness of an exemplary TRPA1 inhibitor in the treatment of nociceptive pain using the following protocol. Male Holtzman rats (approximately 300 grams) may be tested on thermal escape using a Hargreaves type apparatus. Under light anesthesia, a thermal injury (52° C. for 45 seconds) can be applied to one heel. The animals can be tested for thermal escape latency of the injured and uninjured paw before and at 30, 60, 80, and 120 minutes after injury. Drug (a TRPA1 inhibitor) or vehicle (0.5% methylcellulose) can be administered after the baseline measurement and approximately 15-20 minutes prior to the thermal injury. In addition to the escape latency measurement, behavioral observations can be made throughout the experiment.

Example 4

Testing of TRPA1 Antagonists in the Chung Model of Neuropathic Pain

Briefly, male Sprague Dawley rats (approximately 175 grams) can be prepared with ligation of the L4/5 nerve roots. After 5-8 days, the animals can be tested for tactile allodynia using Von Frey hairs. Thresholds can be assessed with the "up-down" method. Drug or vehicle can be administered and the animals can be tested periodically.

INCORPORATION BY REFERENCE

All publications and patents mentioned herein are hereby incorporated by reference in their entirety as if each individual publication or patent was specifically and individually indicated to be incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A method of treating an injury to the skin or respiratory tract on a subject in need thereof resulting from exposure to a chemical warfare agent, the method comprising administering to a subject an effective amount of a compound of Formula (VIII), or a salt thereof:

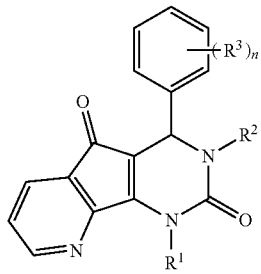

Formula VIII wherein each of $R^1$ and $R^2$ is, independently, H, optionally substituted $C_{1-6}$ alkyl, arylalkyl, heteroarylalkyl, alkoxyalkyl, $COR^{10}$, $CO_2R^{10}$, $CH_2CO_2R^{10}$, or $CONHR^{10}$, where $R^{10}$ is H or optionally substituted $C_{1-6}$ alkyl; each $R^3$ is, independently, hydroxyl, optionally substituted $C_{1-6}$ alkoxy, optionally substituted $C_{1-6}$ alkenyloxy, alkyloxyalkoxy, cyano, acyl, amino, optionally substituted alkylamino, aminoalkyl, amido, acylamino, alkylurea, alkylcarbamoyl, carboxyl, optionally substituted alkylcarboxyl, thioyl, optionally substituted alkylthio, $SO_3H$, optionally substituted alkylsulfinyl, or optionally substituted alkylsulfonyl; and n is 1-3.

2. The method of claim 1, wherein n is 1.

3. The method of claim 1, wherein $R^3$ is alkoxy.

4. The method of claim 1, wherein $R^3$ is alkenyloxy.

5. The method of claim 1, wherein each of $R^1$ and $R^2$ is, independently, H or optionally substituted $C_{1-6}$ alkyl.

6. The method of claim 1, wherein the compound has the Formula IX

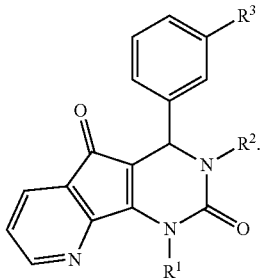

Formula IX

7. The method of claim 1, wherein the compound has the Formula IXa

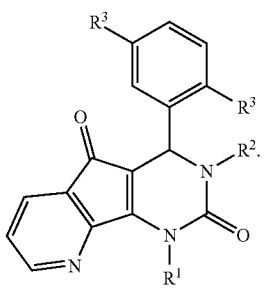

Formula IXa

8. The method of claim 1, wherein the compound is administered after exposure to the chemical warfare agent.

9. The method of claim 1, wherein the subject is a human.

10. The method of claim 1, wherein the injury is inflammation, burn, itch, pain, rash, blisters, sweating, secretions from the mouth, nose, or lung, difficulty breathing, shortness of breath, coughing, phlegm production and narrowing of the airways.

* * * * *